United States Patent
Fennimore et al.

(10) Patent No.: US 10,134,988 B2
(45) Date of Patent: Nov. 20, 2018

(54) SYSTEM FOR FORMING AN ELECTROACTIVE LAYER

(71) Applicant: E. I. DU PONT DE NEMOURS AND COMPANY, Wilmington, DE (US)

(72) Inventors: Adam Fennimore, Wilmington, DE (US); Denis Yurievich Kondakov, Wilmington, DE (US); Nora Sabina Radu, Landenberg, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 15/103,969

(22) PCT Filed: Dec. 11, 2014

(86) PCT No.: PCT/US2014/069795
§ 371 (c)(1),
(2) Date: Jun. 13, 2016

(87) PCT Pub. No.: WO2015/089304
PCT Pub. Date: Jun. 18, 2015

(65) Prior Publication Data
US 2016/0315259 A1 Oct. 27, 2016

Related U.S. Application Data

(60) Provisional application No. 61/915,587, filed on Dec. 13, 2013.

(51) Int. Cl.
*H01L 51/50* (2006.01)
*H01L 51/00* (2006.01)
(Continued)

(52) U.S. Cl.
CPC .......... *H01L 51/0003* (2013.01); *C07C 15/24* (2013.01); *C07F 7/0809* (2013.01);
(Continued)

(58) Field of Classification Search
None
See application file for complete search history.

(56) References Cited

U.S. PATENT DOCUMENTS 6,670,645 B2 12/2003 Grushin
6,875,524 B2 4/2005 Hatwar
(Continued)

FOREIGN PATENT DOCUMENTS

JP 2012-079900 * 4/2012 ............. H01L 51/50
WO 2003040257 A1 5/2003
(Continued)

OTHER PUBLICATIONS

Translation of Foreign Application JP 2012-079900.*
(Continued)

*Primary Examiner* — Abul Kalam

(57) ABSTRACT

There is provided an electroactive system for forming an electroactive layer. The system includes: (a) a first electroactive material; (b) a facilitation additive; and (c) a first liquid medium. The facilitation additive is present during baking in an amount sufficient to enable the electroactive layer made therefrom to effectively resist mixing with a second liquid medium applied thereover after the electroactive system is deposited and baked at a temperature less than 350° C. for a predetermined time.

5 Claims, 5 Drawing Sheets

(51) Int. Cl.
- *H01L 51/56* (2006.01)
- *C07C 15/24* (2006.01)
- *C07F 7/08* (2006.01)
- *C08G 73/02* (2006.01)

(52) U.S. Cl.
CPC ...... *C08G 73/0266* (2013.01); *H01L 51/0007* (2013.01); *H01L 51/0035* (2013.01); *H01L 51/0043* (2013.01); *H01L 51/0058* (2013.01); *H01L 51/0094* (2013.01); *H01L 51/5024* (2013.01); *H01L 51/5056* (2013.01); *H01L 51/56* (2013.01)

(56) References Cited

U.S. PATENT DOCUMENTS

| | | |
|---|---|---|
| 2005/0118455 A1 | 6/2005 | Zhang |
| 2005/0158577 A1 | 7/2005 | Ueda |
| 2007/0063638 A1 | 3/2007 | Funahashi |
| 2007/0292713 A9 | 12/2007 | Herron |
| 2010/0171104 A1* | 7/2010 | Asada .................. H01L 51/0043 257/40 |
| 2011/0095308 A1* | 4/2011 | Chesterfield ............ H01L 31/18 257/79 |
| 2013/0095380 A1 | 4/2013 | Lowe |
| 2013/0248847 A1 | 9/2013 | Fennimore |
| 2013/0299800 A1 | 11/2013 | Merlo |

FOREIGN PATENT DOCUMENTS

| | | |
|---|---|---|
| WO | 2003063555 A1 | 7/2003 |
| WO | 2004016710 A1 | 2/2004 |
| WO | 2007021117 A1 | 2/2007 |
| WO | 2007145979 A2 | 12/2007 |
| WO | 2011053334 A1 | 5/2011 |

OTHER PUBLICATIONS

International Search Report, International Application No. PCT/US2014/069795, International Filing Date: Dec. 11, 2014. dated Apr. 6, 2015.

* cited by examiner

SYSTEM FOR FORMING AN ELECTROACTIVE LAYER

CLAIM OF BENEFIT OF PRIOR APPLICATION

This application claims the benefit of U.S. Provisional Application No. 61/915,587, filed Dec. 13, 2013, which is incorporated in its entirety herein by reference.

BACKGROUND INFORMATION

Field of the Disclosure

The present disclosure relates to novel electroactive systems. The disclosure further relates to electronic devices having at least one active layer made using such an electroactive system.

Description of the Related Art

In organic photoactive electronic devices, such as organic light emitting diodes ("OLED"), that make up OLED displays, one or more electroactive layers are sandwiched between two electrical contact layers. In an OLED, there is an organic photoactive layer which emits light through a light-transmitting electrical contact layer upon application of a voltage across the electrical contact layers.

It is well known to use organic electroluminescent compounds as the photoactive component in light-emitting diodes. Simple organic molecules, conjugated polymers, and organometallic complexes have been used. Devices that use electroluminescent materials frequently include one or more added electroactive layers, which are positioned between the electroluminescent layer and a contact layer. A hole transport layer can be positioned between the electroluminescent layer and the hole-injecting contact layer. The hole-injecting contact layer may also be called the anode. An electron transport layer can be positioned between the electroluminescent layer and the electron-injecting contact layer. The electron-injecting contact layer may also be called the cathode.

There is a continuing need for electroactive layers and ways of forming them for use in electronic devices.

SUMMARY

There is provided an electroactive system for forming an electroactive layer, comprising:
 (a) a first electroactive material;
 (b) a facilitation additive; and
 (c) a first liquid medium;
wherein the facilitation additive is present during baking in an amount sufficient to enable the electroactive layer made therefrom to effectively resist mixing with a second liquid medium applied thereover after the electroactive system is deposited and baked at a temperature less than 350° C. for a predetermined time.

There is also provided a process for forming an electronic device including an electroactive layer formed with the electroactive system.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1A:
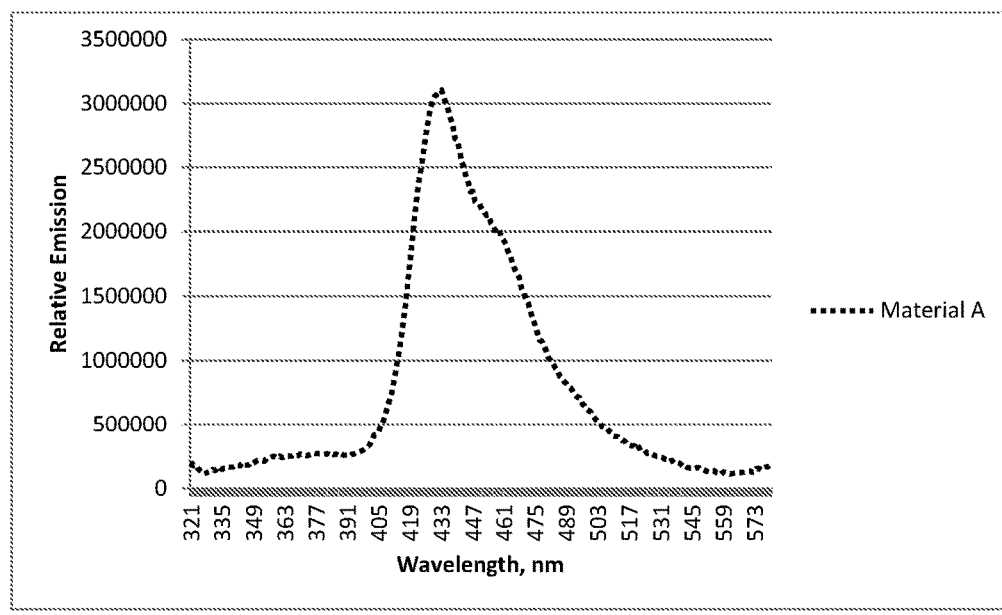
FIG. 1A shows the photoluminescence spectrum of a hole transport material.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

There is provided an electroactive system for forming an electroactive layer, comprising:
 (a) a first electroactive material;
 (b) a facilitation additive; and
 (c) a first liquid medium;
wherein the facilitation additive is present during baking in an amount sufficient to enable the electroactive layer made therefrom to effectively resist mixing with a second liquid medium applied thereover after the electroactive system is deposited and baked at a temperature less than 350° C. for a predetermined time.

There is also provided a process for forming an electronic device including an electroactive layer.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Electroactive System, the Process, the Electronic Device, and finally Examples.

1. Definitions and Clarification of Terms

Before addressing details of embodiments described below, some terms are defined or clarified.

As used herein, the term "alkyl" includes branched and straight-chain saturated aliphatic hydrocarbon groups. Unless otherwise indicated, the term is also intended to include cyclic groups. Examples of alkyl groups include methyl, ethyl, propyl, isopropyl, isobutyl, secbutyl, tertbutyl, pentyl, isopentyl, neopentyl, cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. One example of a substituted alkyl group is trifluoromethyl. Other substituted alkyl groups are formed from one or more of the substituents described herein. In certain embodiments alkyl groups have 1 to 20 carbon atoms. In other embodiments, the group has 1 to 6 carbon atoms. The term is intended to include heteroalkyl groups. Heteroalkyl groups may have from 1-20 carbon atoms.

The term "aryl" means an aromatic carbocyclic moiety, which may be a single ring (monocyclic) or multiple rings (bicyclic, or more) fused together or linked covalently. Any suitable ring position of the aryl moiety may be covalently linked to the defined chemical structure. Examples of aryl moieties include, but are not limited to, phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. In some embodiments, aryl groups have 6 to 60 carbon atoms; in some embodiments, 6 to 30 carbon atoms. The term is intended to include heteroaryl groups. Heteroaryl groups may have from 4-50 carbon atoms; in some embodiments, 4-30 carbon atoms.

The term "alkoxy" is intended to mean the group —OR, where R is alkyl.

The term "aryloxy" is intended to mean the group —OR, where R is aryl.

Unless otherwise indicated, all groups can be substituted or unsubstituted. Exemplary substituents include D, F, alkyl, silyl, alkoxy, siloxy, aryl, aryloxy, deuterated alkyl, deuterated silyl, deuterated alkoxy, deuterated siloxy, deuterated aryl, deuterated aryloxy, and combinations thereof. In some embodiments, substituents are D, F, alkyl, or deuterated alkyl.

The term "bake" and its verb variants refer to the process of exposing a material, member, or structure to a heated environment. The bake temperature is the temperature of the environment. The material, member, or structure may or may not reach the bake temperature.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "compound" is intended to mean an electrically uncharged substance made up of molecules that further include atoms, wherein the atoms cannot be separated from their corresponding molecules by physical means without breaking chemical bonds. The term is intended to include oligomers and polymers.

The term "crosslinking" is intended to mean forming covalent bonds that connect two or more adjacent compounds or polymer chains. The term "crosslinkable group" or "crosslinking group" is intended to mean a group than can lead to crosslinking via thermal treatment or exposure to radiation. In some embodiments, the radiation is UV or visible. Exemplary crosslinkable groups include, but are not limited to vinyl, acrylate, perfluorovinylether, 1-benzo-3,4-cyclobutane, o-quinodimethane groups, siloxane, cyanate groups, cyclic ethers (epoxides), cycloalkenes, and acetylenic groups.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "electroactive" as it refers to a layer or a material, is intended to indicate a layer or material which electronically facilitates the operation of the device. Examples of electroactive materials include, but are not limited to, materials which conduct, inject, transport, or block a charge, where the charge can be either negative (an electron) or positive (a hole), or materials which emit radiation or exhibit a change in concentration of electron-hole pairs when receiving radiation. Examples of inactive materials include, but are not limited to, planarization materials, insulating materials, and environmental barrier materials.

The prefix "fluoro" is intended to indicate that one or more hydrogens in a group has been replaced with fluorine.

The prefix "hetero" indicates that one or more carbon atoms has been replaced with a different atom. In some embodiments, the heteroatom is O, N, S, or combinations thereof.

The term "host material" is intended to mean a matrix material which is used in a photoactive layer with a dopant. The host material may or may not have electronic characteristic(s) or the ability to emit, receive, or filter radiation. The host material is present in larger concentration than the dopant in the photoactive layer.

The term "liquid composition" is intended to mean a liquid medium in which a material is dissolved to form a solution, a liquid medium in which a material is dispersed to form a dispersion, or a liquid medium in which a material is suspended to form a suspension or an emulsion.

The term "liquid medium" is intended to mean a liquid material, including a pure liquid and a combination of liquids. Liquid medium is used in the singular, regardless of whether one or more solvents are present.

The term "photoactive" is intended to mean a material that emits light when activated by an applied voltage (such as in a light emitting diode or chemical cell) or responds to radiant energy and generates a signal with or without an applied bias voltage (such as in a photodetector or a photovoltaic cell).

The term "polymer" is intended to mean a material having at least one repeating monomeric unit. The term includes homopolymers having only one kind of monomeric unit, and copolymers having two or more different monomeric units. Copolymers are a subset of polymers. In some embodiments, a polymer has at least 5 repeating units; in some embodiments, at least 10 repeating units; in some embodiments, at least 20 repeating units. In some embodiments, a polymer has a number average molecular weight greater than 10,000. In some embodiments, a polymer has a number average molecular weight greater than 50,000. In some embodiments, a polymer has a number average molecular weight greater than 100,000.

The term "siloxane" refers to the group $(RO)_{1-3}(R')_{2-0}Si—$, where R and R' are the same or different and are H, D, C1-20 alkyl, fluoroalkyl, deuterated alkyl, or deuterated fluoroalkyl.

The term "siloxy" refers to the group $R_3SiO—$, where R is H, D, C1-20 alkyl, fluoroalkyl, aryl, deuterated alkyl, deuterated fluoroalkyl, or deuterated aryl. In some embodiments, one or more carbons in an R alkyl group are replaced with Si.

The term "silyl" refers to the group $R_3Si—$, where R is H, D, C1-20 alkyl, fluoroalkyl, aryl, deuterated alkyl, deuterated fluoroalkyl, or deuterated aryl. In some embodiments, one or more carbons in an R alkyl group are replaced with Si. In some embodiments, the silyl groups are (hexyl)$_2$Si(Me)CH$_2$CH$_2$Si(Me)$_2$- and [CF$_3$(CF$_2$)$_6$CH$_2$CH$_2$]$_2$SiMe-.

The term "workpiece" is intended to mean a substrate at any particular point of a process sequence. Note that the substrate may not significantly change during a process sequence, whereas the workpiece significantly changes during the process sequence. For example, at a beginning of a process sequence, the substrate and workpiece are the same. After a layer is formed over the substrate, the substrate has not changed, but now the workpiece includes the substrate and the layer.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

Unless otherwise indicated, all groups can be unsubstituted or substituted. In some embodiments, the substituents are selected from the group consisting of deuterium, halide, alkyl, alkoxy, aryl, amino, silyl, and cyano.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Electroactive System

As used herein, the term "electroactive system" is intended to mean the components necessary to form an electroactive layer in a device, by liquid deposition.

In some embodiments, the electroactive system includes an electroactive material, a facilitation additive, and a first liquid medium, wherein the facilitation additive is in juxtaposition with the electroactive material when the electroactive layer is formed. By "juxtaposition with" it is meant that the facilitation additive is close enough to the electroactive material to affect the formation of the electroactive layer.

In some embodiments, the electroactive system is a composition including the electroactive material, the facilitation additive, and the first liquid medium.

In some embodiments, the electroactive system is a composition including only the electroactive material, the facilitation additive, and the first liquid medium, where components that would materially alter the function, the principle of operation, or the distinguishing characteristics of the composition are not present.

In some embodiments, the electroactive material is present in the first liquid medium, and the facilitation additive is present as a separate layer.

In some embodiments, the electroactive material is present in the first liquid medium, and the facilitation additive is present in the vapor state.

In some embodiments, the electroactive material is a polymer.

In some embodiments, the electroactive material is an oligomer.

In some embodiments, the electroactive material is a small molecule.

In some embodiments, the electroactive material is a small molecule having at least one crosslinkable group.

In some embodiments, the electroactive material includes a hole transport material.

In some embodiments, the electroactive material includes a photoactive material.

In some embodiments, the electroactive material includes at least one photoactive material and at least one host material.

(a) Hole Transport Material

In some embodiments, the first electroactive material includes hole transport material.

Any material having hole transport properties can be used in the hole transport system.

In some embodiments, the hole transport material is a small molecule. In some embodiments, the small molecule has a molecular weight less than 1000.

In some embodiments, the hole transport material is an oligomer having 2-5 repeating units.

In some embodiments, the hole transport material is a hole transport polymer, which can be a homopolymer or a copolymer.

In some embodiments, the hole transport polymer has crosslinkable groups.

In some embodiments, the hole transport polymer has no crosslinkable groups.

In some embodiments, the hole transport material is deuterated. The term "deuterated" is intended to mean that at least one H has been replaced by D. The term "deuterated analog" refers to a structural analog of a material or group in which one or more available hydrogens have been replaced with deuterium. In a deuterated material or deuterated analog, the deuterium is present in at least 100 times the natural abundance level. In some embodiments, the material is at least 10% deuterated. By "% deuterated" or "% deuteration" is meant the ratio of deuterons to the sum of protons plus deuterons, expressed as a percentage. In some embodiments, the material is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated. In a hole transport oligomer or polymer, the deuteration can be present throughout the oligomer or polymer, on the backbone chain, or on substituent groups.

In some embodiments, the hole transport material has one or more groups selected from the group consisting of arylamino, carbazole, and combinations thereof. In a hole transport oligomer or polymer, the groups can be present as part of the backbone chain or as side chains.

In some embodiments, the hole transport material is an oligomer or polymer having multiple arylamino groups and multiple fluorene groups.

In some embodiments, the hole transport material is a copolymer of one or more arylamino monomers and one or more fluorene monomers.

In some embodiments, the hole transport material has Formula I

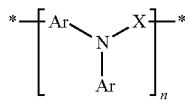

(I)

wherein:
Ar is the same or different at each occurrence and is an aryl or deuterated aryl group;
X is the same or different at each occurrence and is selected from the group consisting of a single bond, an aryl group, and a deuterated aryl group;
n is an integer greater than 0; and
* represents a point of attachment, H, D, halide, aryl, or deuterated aryl;
with the proviso that when n=1, X=aryl or deuterated aryl.
Exemplary aryl groups include phenyl, naphthyl, anthracenyl, combinations of such groups linked together covalently, and deuterated analogs thereof.

In some embodiment, the hole transport material has Formula II

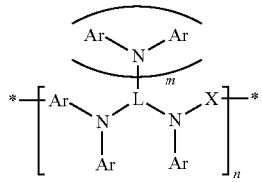

(II)

wherein:
L is the same or different at each occurrence and is selected from the group consisting of aryl, $(CR'_2)_c$, adamantyl, bicyclic cyclohexyl, a bicyclic group having aliphatic rings connected through a single atom, and deuterated analogs thereof;
R' is the same or different at each occurrence and is selected from the group consisting of H, D, alkyl, fluoroalkyl, aryl, deuterated alkyl, deuterated fluoroalkyl, and deuterated aryl;
c is 1-5;
m is 0, 1, or 2; and
Ar, X, n and * are as defined above.

In some embodiments, L is selected from the group consisting of polycyclic aromatic groups, two or more polycyclic aromatic groups joined by single bonds, substituted analogs thereof, deuterated analogs thereof, and substituted deuterated analogs thereof.

In some embodiments, L is selected from the group consisting of phenyl, naphthyl, anthryl, biphenyl, binaphthyl, anthryl, bianthryl, substituted analogs thereof, deuterated analogs thereof, substituted deuterated analogs thereof, and two or more such groups joined together by single bonds.

In some embodiments, L is selected from the group consisting of phenyl, naphthyl, anthryl, biphenyl, binaphthyl, anthryl, bianthryl, substituted analogs thereof, deuterated analogs thereof, and substituted deuterated analogs thereof.

In some embodiments, the hole transport material is a copolymer having Formula III

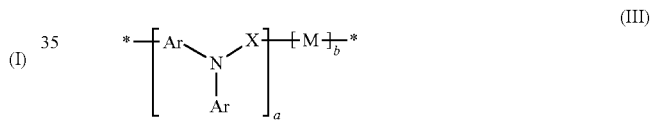

(III)

wherein:
M is the same or different at each occurrence and is an aromatic monomer unit or deuterated aromatic monomer unit,
a and b are relative mole fractions, such that a+b=1, and
Ar, X and * are as defined above.
In some embodiments, M is selected from the group consisting of fluorene, spirobifluorene, triarylamines, carbazole, one or more carbocyclic groups linked together covalently, where the carbocyclic groups are selected from the group consisting of phenyl, naphthyl, anthracenyl, deuterated analogs thereof, and combinations thereof.

In some embodiments, the hole transport material is a copolymer having Formula IV

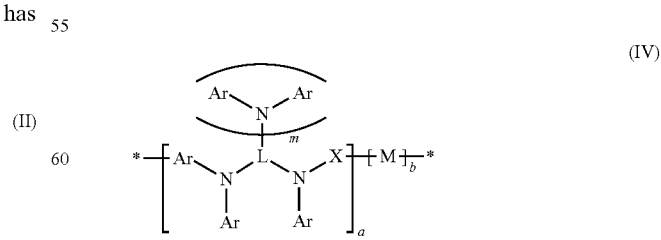

(IV)

wherein the Ar, L, M, X, a, b, m and * are as defined above.
In some embodiments, the hole transport material has Formula V

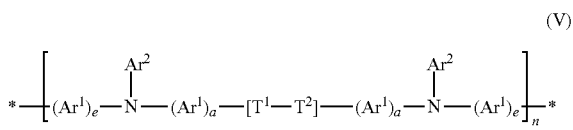

where:
- $Ar^1$ is the same or different at each occurrence and is selected from the group consisting of phenylene, substituted phenylene, naphthylene, substituted naphthylene, and deuterated analogs thereof;
- $Ar^2$ is the same or different at each occurrence and is an aryl group or deuterated aryl group;
- M is the same or different at each occurrence and is a conjugated moiety or deuterated conjugated moiety;
- $T^1$ and $T^2$ are independently the same or different at each occurrence and are conjugated moieties which are connected in a non-planar configuration, or a deuterated analog thereof;
- a is the same or different at each occurrence and is an integer from 1 to 6;
- e is the same or different at each occurrence and is an integer from 1 to 6;
- n is an integer greater than 0; and
- * represents a point of attachment, H, D, halide, aryl, or deuterated aryl.

In some embodiment, the hole transport polymer has Formula VI

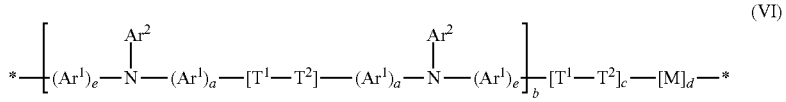

wherein:
- M is the same or different at each occurrence and is a conjugated moiety or deuterated conjugated moiety;
- b, c, and d are mole fractions such that b+c+d=1.0, with the proviso that c is not zero, and at least one of b and d is not zero, and when b is zero, M comprises at least two triarylamine units; and
- $Ar^1$, $Ar^2$, $T^1$, $T^2$, a, e, and * are as defined above.

In some embodiments of Formula V or Formula VI, $[T^1-T^2]$ is a substituted biphenylene group or deuterated analog thereof. The term "biphenylene" is intended to mean a biphenyl group having two points of attachment to the compound backbone. The term "biphenyl" is intended to mean a group having two phenyl units joined by a single bond. The biphenylene group can be attached at one of the 2, 3-, 4-, or 5-positions and one of the 2', 3'-, 4'-, or 5'-positions. The substituted biphenylene group has at least one substituent in the 2-position. In some embodiments, the biphenylene group has substituents in at least the 2- and 2'-positions. In some embodiments, the substituents are alkyl groups, aryl groups, or deuterated analogs thereof In some embodiments, $[T^1-T^2]$ is a binaphthylene group or deuterated binaphthylene group. The term "binaphthylene" is intended to mean a binapthyl group having 2 points of attachment to the compound backbone. The term "binaphthyl" is intended to mean a group having two naphthalene units joined by a single bond. In some embodiments, the binaphthylene group is a 1,1'-binaphthylene, which is attached to the compound backbone at one of the 3-, 4-, 5-, 6, or 7-positions and one of the 3'-, 4'-, 5'-, 6', or 7'-positions. This is illustrated below, where the dashed lines represent possible points of attachment.

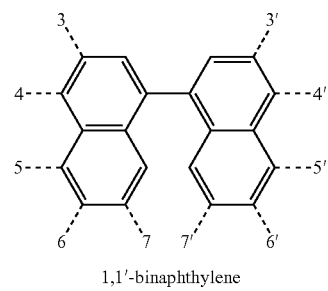

1,1'-binaphthylene

In some embodiments, the binaphthylene group is a 1,2'-binaphthylene having at least one substituent at the 8- or 9'-position, and which is attached to the compound backbone at one of the 3-, 4-, 5-, 6, or 7-positions and one of the 4'-, 5'-, 6'-, 7', or 8'-positions. This is illustrated below, where the dashed lines represent possible points of attachment and at least one R represents a substituent.

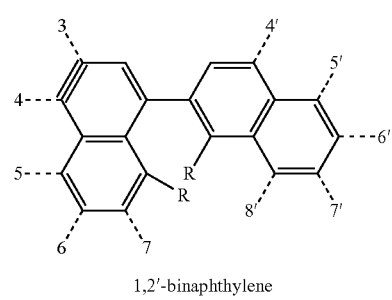

1,2'-binaphthylene

In some embodiments, the binaphthylene group is a 2,2'-binaphthylene having at least one substituent at the 8- or 9'-position, and which is attached to the compound backbone at one of the 4-, 5-, 6-, 7, or 8-positions and one of the 4'-, 5'-, 6'-, 7', or 8'-positions. This is illustrated below, where the dashed lines represent possible points of attachment and at least one R represents a substituent.

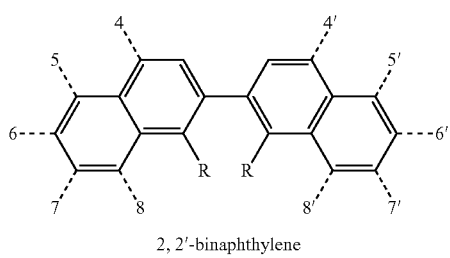

2, 2'-binaphthylene

In some embodiments, [T¹-T²] is a phenylene-naphthylene group, or deuterated phenylene-naphthylene group. In some embodiments, [T¹-T²] is a phenylene-1-naphthylene group, which is attached to the compound backbone at one of the 3-, 4-, or 5-positions in the phenylene and one of the 3-, 4-, or 5-positions of the naphthylene. In some embodiments, [T¹-T²] is a phenylene-2-naphthylene group, which is attached to the compound backbone at one of the 3-, 4-, or 5-positions in the phenylene and one of the 4-, 5-, 6-, 7-, or 8-positions of the naphthylene.

In some embodiments, the biphenylene, binaphthylene, and phenylene-naphthylene groups are substituted at one or more positions.

In some embodiments, [T¹-T²] is selected from one of the following:

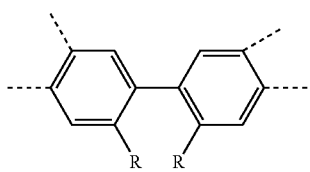

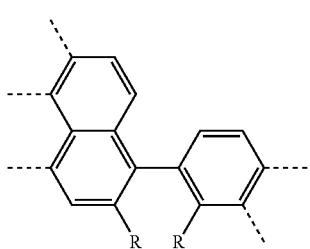

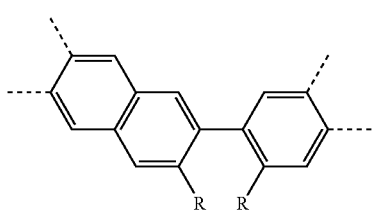

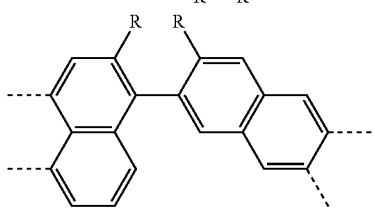

-continued

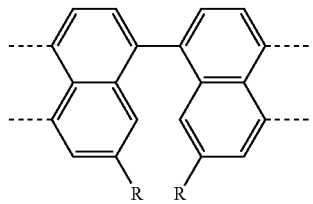

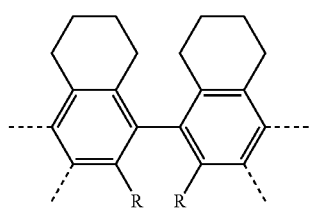

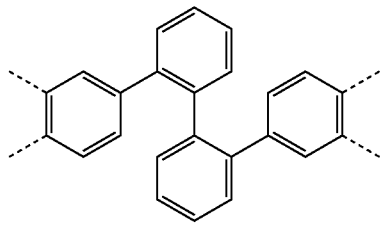

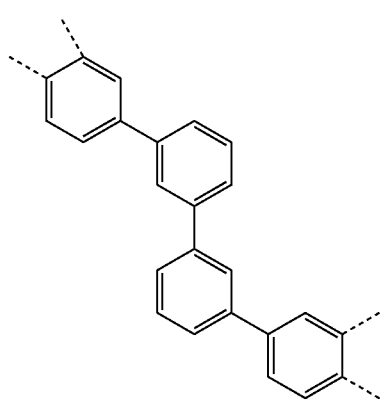

where R is the same or different and is selected from the group consisting of alkyl, aryl, alkoxy, aryloxy, fluoroalkyl, fluoroaryl, fluoroaryloxy fluoroalkyloxy, oxyalkyl, alkenyl groups, silyl, siloxane, and deuterated analogs thereof. Any of the above groups may also be deuterated.

In some embodiments, the hole transport material has Formula VII

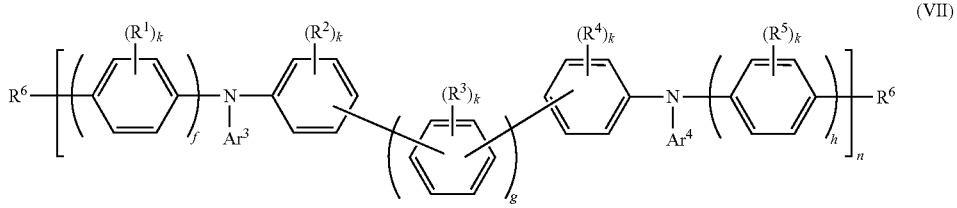

(VII)

wherein:
Ar$^1$ and Ar$^2$ are the same or different and are aryl groups or deuterated aryl groups;
R$^1$ through R$^5$ are independently the same or different at each occurrence and are selected from the group consisting of D, F, alkyl, aryl, alkoxy, silyl, a crosslinkable group, deuterated alkyl, deuterated aryl, deuterated alkoxy, deuterated silyl, and a deuterated crosslinkable group;
R$^6$ is the same or different at each occurrence and is selected from the group consisting of H, D, and halogen;
k is the same or different at each occurrence and is an integer from 0 to 4;
f is 1 or 2;
g is 0, 1 or 2;
h is 1 or 2; and
n is an integer greater than 0.

Any of the above embodiments of the hole transport polymer can be combined with one or more of the other embodiments, so long as they are not mutually exclusive. For example, the embodiment in which the hole transport material is a polymer can be combined with the embodiment in which the hole transport material is deuterated and the embodiment in which the hole transport material has Formula I and Ar is phenyl. The same is true for the other non-mutually-exclusive embodiments discussed above. The skilled person would understand which embodiments were mutually exclusive and would thus readily be able to determine the combinations of embodiments that are contemplated for the hole transport polymer in the present application.

(b) Photoactive Material

In some embodiments, the first electroactive material includes photoactive material.

In some embodiments, the first electroactive material includes only photoactive material, where components that would materially alter the function, the principle of operation, or the distinguishing characteristics of the material are not present.

In some embodiments, the first electroactive material is a composition including (a) a host compound and (b) a photoactive dopant capable of electroluminescence having an emission maximum between 380 and 750 nm. In some embodiments, the composition includes only (a) a host compound and (b) a photoactive dopant capable of electroluminescence having an emission maximum between 380 and 750 nm, where components that would materially alter the principle of operation or the distinguishing characteristics of the composition are not present.

In some embodiments, the first electroactive material is a composition including (a) a first host compound, (b) a photoactive dopant capable of electroluminescence having an emission maximum between 380 and 750 nm, and (c) a second host material. In some embodiments, the composition includes only (a) a first host compound, (b) a photoactive dopant capable of electroluminescence having an emission maximum between 380 and 750 nm, and (c) a second host material, where components that would materially alter the principle of operation or the distinguishing characteristics of the composition are not present.

The amount of photoactive dopant present in the composition is generally in the range of 3-20% by weight, based on the total weight of the composition; in some embodiments, 5-15% by weight. When a second host is present, the ratio of first host to second host is generally in the range of 1:20 to 20:1; in some embodiments, 5:15 to 15:5.

Electroluminescent ("EL") materials which can be used as a photoactive dopant include, but are not limited to, small molecule organic luminescent compounds, luminescent metal complexes, conjugated polymers, and mixtures thereof. Examples of small molecule luminescent organic compounds include, but are not limited to, chrysenes, pyrenes, perylenes, rubrenes, coumarins, anthracenes, thiadiazoles, benzofluorenes, derivatives thereof, deuterated analogs thereof, and mixtures thereof. Examples of metal complexes include, but are not limited to, metal chelated oxinoid compounds, cyclometallated complexes of metals such as iridium and platinum, and deuterated analogs thereof. Examples of conjugated polymers include, but are not limited to poly(phenylenevinylenes), polyfluorenes, poly(spirobifluorenes), polythiophenes, poly(p-phenylenes), copolymers thereof, deuterated analogs thereof, and mixtures thereof.

Examples of red light-emitting materials include, but are not limited to, complexes of Ir having phenylquinoline or phenylisoquinoline ligands, periflanthenes, fluoranthenes, and perylenes. Red light-emitting materials have been disclosed in, for example, U.S. Pat. No. 6,875,524, and published US application 2005-0158577.

Examples of green light-emitting materials include, but are not limited to, complexes of Ir having phenylpyridine ligands, bis(diarylamino)anthracenes, and polyphenylenevinylene polymers. Green light-emitting materials have been disclosed in, for example, published PCT application WO 2007/021117.

Examples of blue light-emitting materials include, but are not limited to, complexes of Ir having phenylpyridine or phenylimidazole ligands, diarylanthracenes, diaminochrysenes, diaminopyrenes, and polyfluorene polymers. Blue light-emitting materials have been disclosed in, for example, U.S. Pat. No. 6,875,524, and published US applications 2007-0292713 and 2007-0063638.

In some embodiments, the photoactive dopant is an organometallic complex. In some embodiments, the organometallic complex is cyclometallated. By "cyclometallated" it is meant that the complex contains at least one ligand which bonds to the metal in at least two points, forming at least one 5- or 6-membered ring with at least one carbon-metal bond. In some embodiments, the metal is iridium or platinum. In some embodiments, the organometallic complex is electrically neutral and is a tris-cyclometallated complex of iridium having the formula IrL₃ or a bis-cyclometallated complex of iridium having the formula IrL₂Y. In some embodiments, L is a monoanionic bidentate cyclometalating ligand coordinated through a carbon atom and a nitrogen atom. In some embodiments, L is an aryl N-heterocycle, where the aryl is phenyl or napthyl, and the N-heterocycle is pyridine, quinoline, isoquinoline, diazine, pyrrole, pyrazole or imidazole. In some embodiments, Y is a monoanionic bidentate ligand. In some embodiments, L is a phenylpyridine, a phenylquinoline, or a phenylisoquinoline. In some embodiments, Y is a β-dienolate, a diketimine, a picolinate, or an N-alkoxypyrazole. The ligands may be unsubstituted or substituted with F, D, alkyl, perfluororalkyl, alkoxyl, alkylamino, arylamino, CN, silyl, fluoroalkoxyl or aryl groups.

In some embodiments, the photoactive dopant is a cyclometalated complex of iridium or platinum. Such materials have been disclosed in, for example, U.S. Pat. No. 6,670,645 and Published PCT Applications WO 03/063555, WO 2004/016710, and WO 03/040257.

In some embodiments, the photoactive dopant is a complex having the formula $Ir(L1)_a(L2)_b(L3)_c$; where
 L1 is a monoanionic bidentate cyclometalating ligand coordinated through carbon and nitrogen;
 L2 is a monoanionic bidentate ligand which is not coordinated through a carbon;
 L3 is a monodentate ligand;
 a is 1-3;
 b and c are independently 0-2; and
 a, b, and c are selected such that the iridium is hexacoordinate and the complex is electrically neutral.

Some examples of formulae include, but are not limited to, $Ir(L1)_3$; $Ir(L1)_2(L2)$; and $Ir(L1)_2(L3)(L3')$, where L3 is anionic and L3' is nonionic.

Examples of L1 ligands include, but are not limited to phenylpyridines, phenylquinolines, phenylpyrimidines, phenylpyrazoles, thienylpyridines, thienylquinolines, and thienylpyrimidines. As used herein, the term "quinolines" includes "isoquinolines" unless otherwise specified. The fluorinated derivatives can have one or more fluorine substituents. In some embodiments, there are 1-3 fluorine substituents on the non-nitrogen ring of the ligand.

Monoanionic bidentate ligands, L2, are well known in the art of metal coordination chemistry. In general these ligands have N, O, P, or S as coordinating atoms and form 5- or 6-membered rings when coordinated to the iridium. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and phosphinoalkanols (phosphinoalkoxide ligands).

Monodentate ligand L3 can be anionic or nonionic. Anionic ligands include, but are not limited to, H⁻ ("hydride") and ligands having C, O or S as coordinating atoms. Coordinating groups include, but are not limited to alkoxide, carboxylate, thiocarboxylate, dithiocarboxylate, sulfonate, thiolate, carbamate, dithiocarbamate, thiocarbazone anions, sulfonamide anions, and the like. In some cases, ligands listed above as L2, such as β-enolates and phosphinoakoxides, can act as monodentate ligands. The monodentate ligand can also be a coordinating anion such as halide, cyanide, isocyanide, nitrate, sulfate, hexahaloantimonate, and the like. These ligands are generally available commercially.

The monodentate L3 ligand can also be a non-ionic ligand, such as CO or a monodentate phosphine ligand.

In some embodiments, one or more of the ligands has at least one substituent selected from the group consisting of F and fluorinated alkyls. The iridium complex dopants can be made using standard synthetic techniques as described in, for example, U.S. Pat. No. 6,670,645.

In some embodiments, the photoactive dopant is a small organic luminescent compound. In some embodiments, the photoactive dopant is selected from the group consisting of a non-polymeric spirobifluorene compound and a fluoranthene compound.

In some embodiments, the photoactive dopant is a compound having aryl amine groups. In some embodiments, the photoactive dopant is selected from the formulae below:

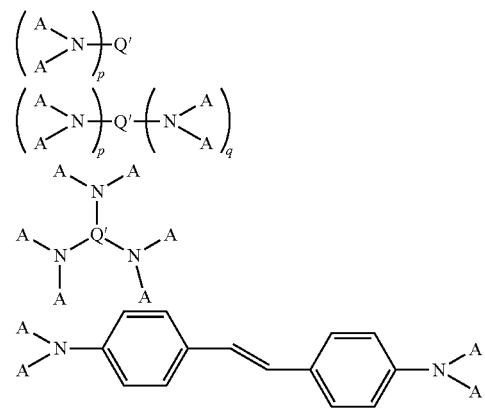

where:
 A is the same or different at each occurrence and is an aromatic group having from 3-60 carbon atoms;
 Q' is a single bond or an aromatic group having from 3-60 carbon atoms;
 p and q are independently an integer from 1-6.

In some embodiments of the above formula, at least one of A and Q' in each formula has at least three condensed rings. In some embodiments, p and q are equal to 1.

In some embodiments, Q' is a styryl or styrylphenyl group.

In some embodiments, Q' is an aromatic group having at least two condensed rings. In some embodiments, Q' is selected from the group consisting of naphthalene, anthracene, chrysene, pyrene, tetracene, xanthene, perylene, coumarin, rhodamine, quinacridone, and rubrene.

In some embodiments, A is selected from the group consisting of phenyl, biphenyl, tolyl, naphthyl, naphthylphenyl, and anthracenyl groups.

In some embodiments, the photoactive dopant has the formula below:

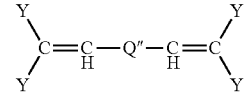

where:

Y is the same or different at each occurrence and is an aromatic group having 3-60 carbon atoms;

Q" is an aromatic group, a divalent triphenylamine residue group, or a single bond.

In some embodiments, the photoactive dopant is an aryl acene. In some embodiments, the photoactive dopant is a non-symmetrical aryl acene.

In some embodiments, the photoactive dopant is a chrysene derivative. The term "chrysene" is intended to mean 1,2-benzophenanthrene. In some embodiments, the photoactive dopant is a chrysene having aryl substituents. In some embodiments, the photoactive dopant is a chrysene having arylamino substituents. In some embodiments, the photoactive dopant is a chrysene having two different arylamino substituents. In some embodiments, the chrysene derivative has a deep blue emission.

In some embodiments, the host material is a small molecule.

In some embodiments, the host compound is selected from the group consisting of indolocarbazoles, chrysenes, phenanthrenes, triphenylenes, phenanthrolines, triazines, naphthalenes, anthracenes, quinolines, isoquinolines, quinoxalines, phenylpyridines, benzodifurans, metal quinolinate complexes, deuterated analogs thereof, and combinations thereof.

In some embodiments, the host material is selected from the group consisting of anthracenes, chrysenes, pyrenes, phenanthrenes, triphenylenes, phenanthrolines, naphthalenes, triazines, quinolines, isoquinolines, quinoxalines, phenylpyridines, benzodifurans, metal quinolinate complexes, indolocarbazoles, deuterated analogs thereof, and combinations thereof.

In some embodiments, the host material is a 9,10-diaryl anthracene compound or deuterated analog thereof.

In some embodiments, the host material is a chrysene derivative having one or two diarylamino substituents, or a deuterated analog thereof.

(c) Facilitation Additive

The facilitation additive aids in the formation of the electroactive layer. The electroactive layer is formed by liquid deposition of the electroactive material in the first liquid medium, followed by baking at a predetermined temperature less than 350° C., for a predetermined time. The facilitation additive is present during baking of the electroactive layer in an amount sufficient to increase the solvent resistance of the thus-formed electroactive layer.

In some embodiments, the facilitation additive is a small molecule. In some embodiments, the small molecule has a molecular weight less than 2000; in some embodiments, less than 1000; in some embodiments, less than 750.

In some embodiments, the facilitation additive is an oligomer. In some embodiments, the oligomer has a number average molecular weight between 2000 and 10,000; in some embodiments, between 2000 and 4000.

In some embodiments, the facilitation additive is a polymer.

In some embodiments, the facilitation additive has no crosslinkable groups.

In some embodiments, the facilitation additive has a boiling point of 150° C. or greater; in some embodiments, 200° C. or greater; in some embodiments, 250° C. or greater; in some embodiments, 300° C. or greater; in some embodiments, 350° C. or greater.

In some embodiments, the facilitation additive has a vapor pressure at 200° C. that is in the range of $10^{-3}$ Pa to 40 Pa; in some embodiments, $10^{-2}$ Pa to 20 Pa; in some embodiments, 0.1 Pa to 1.0 Pa; in some embodiments, 0.1 Pa to 0.8 Pa.

In some embodiments, the facilitation additive has a vapor pressure at 225° C. that is in the range of $10^{-3}$ Pa to 40 Pa; in some embodiments, $10^{-2}$ Pa to 20 Pa; in some embodiments, 0.1 Pa to 1.0 Pa; in some embodiments, 0.1 Pa to 0.8 Pa.

In some embodiments, the facilitation additive is a material which passes the Photoluminescent Test ("PLT"), described in detail in the Examples. In the PLT, a change in photoluminescence is used as an indication of mixing between layers.

In the PLT, a first material is deposited on a substrate from a liquid composition, and baked at a predetermined temperature for a predetermined time, to form a first layer. A second liquid composition including a second material is then deposited over the first layer and baked to form a second layer. Both the first and second materials are photoluminescent at a given wavelength.

The second material is photoluminescent at higher energy and its emission is sufficiently distinct to be identified when present in combination with the emission of the second material. When molecules of the first material are adjacent to the molecules of the second material (as in a homogeneous mixture), excitation of the second material results in energy transfer to the first material such that the only emission from the first material is detectable. Such energy transfer is called quenching. Similarly, when molecules of the second material are not immediately adjacent, but separated from the molecules of the first material by several nanometers distance of, for example, some inert buffer material, the emission of the second material is partly quenched. Assuming that first and second materials are excited uniformly, the resultant emission in such case is comprised of two components and a relative amount of second material emission is a function of distance between the layers and, in mixed layers, concentration of the first material. Typically, the maximum separation distance of 5-10 nm is sufficient to ensure that quenching is negligible regardless of the concentration of the first material. Considering practical case of two layers of the first and second material without any additional buffer between them, only that part of the second material layer that is further away from the first layer (or mixed region) than such distance would be completely unquenched. In practical implementation of the test, it is suitable to choose the nominal thickness of the second layer larger than such distance. In this case it follows that the observation of the substantial photoluminescence of the second material indicates that the substantial part of second material layer is unmixed. In contrast, an absence of significant photoluminescence of the second material indicates significant mixing of the layers.

Figure 1B:
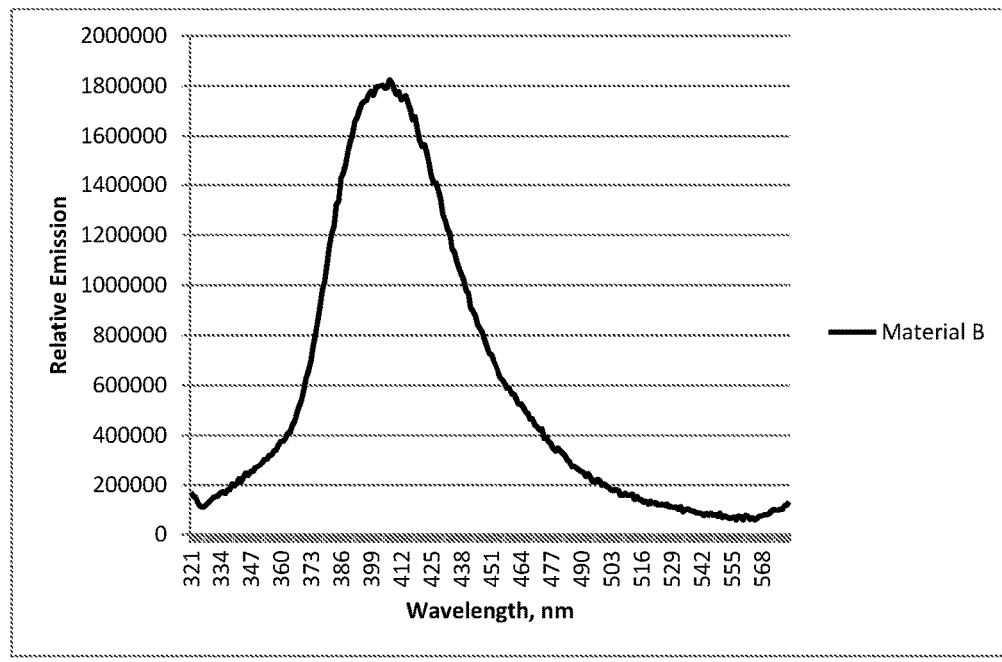
FIG. 1B shows the photoluminescence spectrum of an emissive material.
Figure 2A:
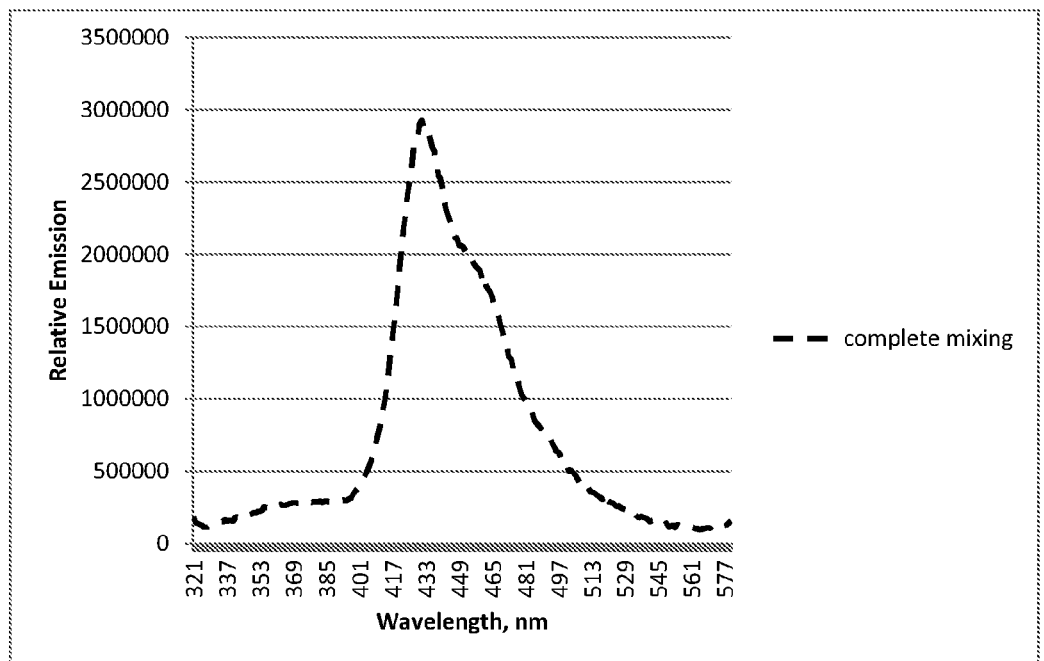
FIG. 2A shows the photoluminescence spectrum resulting from one Photoluminescence Test.
Figure 2B:
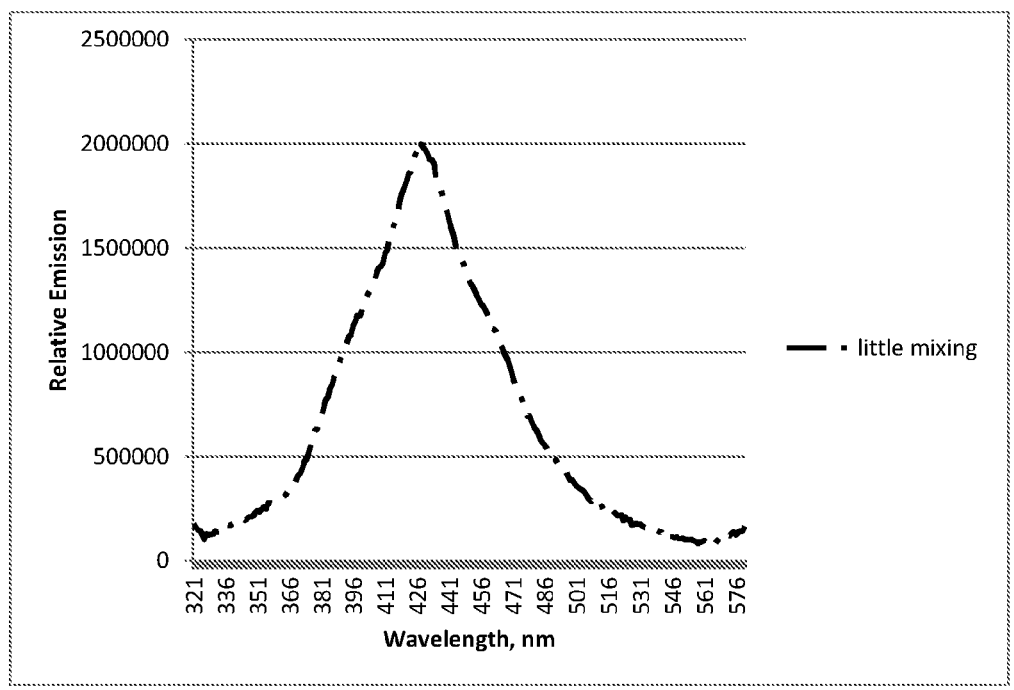
FIG. 2B shows the photoluminescence spectrum resulting from another Photoluminescence Test.
Figure 3:
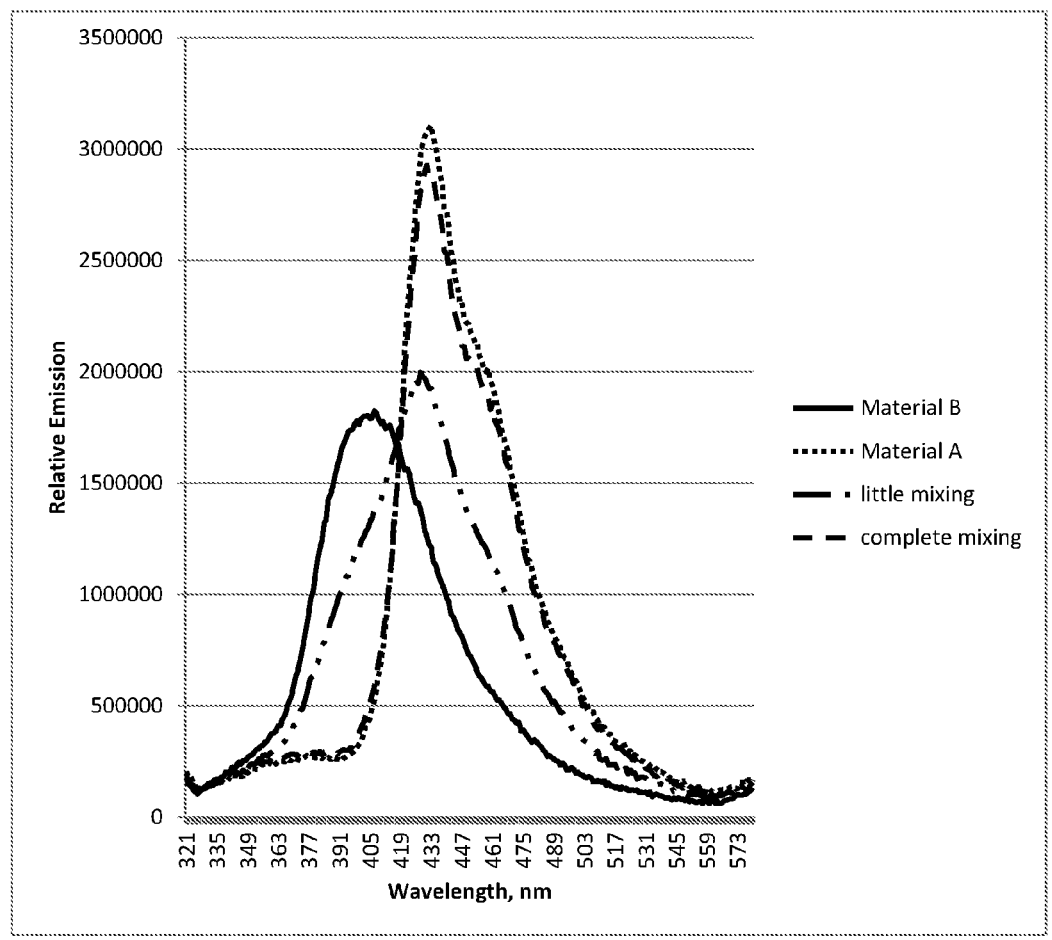
FIG. 3 shows the overlay of the spectra from FIGS. 1-2.

The PLT is illustrated in FIGS. 1-3. Photoluminescent hole transport material A in a liquid composition is deposited on a substrate, and exposed to a predetermined temperature for a predetermined time. The photoluminescent spectrum of material A alone, when excited by light having a wavelength λ1, is shown in FIG. 1A. A photoactive layer is then formed over the hole transport layer by liquid deposition of a solution of a photoluminescent photoactive material B. The photoluminescent spectrum of material B alone, when excited by light having wavelength λ1, is shown in FIG. 1B. It can be seen that the spectra are distinguishable and that the spectrum of material A has a maximum at a longer wavelength and thus lower energy. These layers are then encapsulated. The encapsulated composite is then excited by light having wavelength λ1. If the hole transport layer is not resistant to the liquid medium for the photoactive material, then the two layers will be mixed and the resulting spectrum will be very similar to that of material A alone. The higher energy photoluminescence from material B will be quenched by material A. This is shown in FIG. 2A. If the hole transport layer is resistant to the liquid medium for the photoactive material, then two discrete layers will be formed and the resulting spectrum will have a shape that is a combination or blend of the peaks for both materials. This is shown in FIG. 2B. FIG. 3 shows the overlay of all four spectra from the first four figures. It is clear that the spectrum representing little mixing is a composite of the individual spectra of material A and material B. It is clear that when mixing is complete, only the spectrum of the lower energy material A is seen.

A material which passes the PLT is one which, when added to the hole transport layer in a predetermined amount, results in a composite having a photoluminescence spectrum which is a blend of the spectra for both materials A and B.

It will be appreciated that some materials may pass the PLT at higher temperatures, but not at lower temperatures. Some materials may pass the PLT in higher concentration, but not at lower concentration.

In some embodiments, the facilitation additive is a material which passes the Spun Coat OLED Test ("SCOLEDT"), described in detail in the examples.

In a SCOLEDT a light emitting diode is formed where two or more electroactive layers are deposited via spincasting. Layers in the light emitting diode not formed by spincasting may be formed by a variety of physical vapor deposition techniques (sputtering, thermal evaporation, etc.) A facilitation additive may or may not be present during the baking of the first of the two spuncast layers.

The device performance (efficiency, stability, voltage, and color) of devices which employed facilitation additives during the bake of the first layer is compared to the performance of devices formed without facilitation additives where the first layer is baked at the same conditions (temperature and time) or at the champion bake conditions (typically a higher temperature). Effectiveness of the facilitation additive is determined by how much the performance of the test device using facilitation additives exceeds that of the devices baked at the same conditions without facilitation additives. For some facilitation additives the test device performance will even match (or exceed) that of the champion devices.

In some embodiments the layer which employs facilitation additives is a hole transport layer (HTL) and the subsequent layer is a light emissive layer (EML).

In some embodiments, the facilitation additive is a material which passes the Nozzle Printed OLED Test ("NPOLEDT"), described below In a NPOLEDT light emitting diodes are formed where of two or more electroactive layers deposited from solution at least one is formed via nozzle printing. Nozzle printing is a commercially viable process for patterning OLEDs for display applications. Layers in the light emitting diodes not deposited from solution may be formed by a variety of physical vapor deposition techniques (sputtering, thermal evaporation, etc.). A facilitation additive may or may not be present during the baking of the first of the two solution deposited layers.

The device performance (efficiency, stability, voltage, and color) of devices which employed facilitation additives during the bake of the first layer is compared to the performance of devices formed without facilitation additives where the first layer is baked at the same conditions (temperature and time) or at the champion bake conditions (typically a higher temperature). Effectiveness of the facilitation additive is determined by how much the performance of the test device using facilitation additives exceeds that of the devices baked at the same conditions without facilitation additives. For some facilitation additives the test device performance will even match (or exceed) that of the champion devices.

In some embodiments the layer which employs facilitation additives is a hole transport layer (HTL) and the subsequent layer is a light emissive layer (EML).

In some embodiments, the facilitation additive is a material which passes the Inkjet Printed OLED Test ("IJPOLEDT"), described below In a IJPOLEDT light emitting diodes are formed where of two or more electroactive layers deposited from solution at least one is formed via inkjet printing. Inkjet printing is a commercially viable process for patterning OLEDs for display applications. Layers in the light emitting diodes not deposited from solution may be formed by a variety of physical vapor deposition techniques (sputtering, thermal evaporation, etc.). A facilitation additive may or may not be present during the baking of the first of the two solution deposited layers.

The device performance (efficiency, stability, voltage, and color) of devices which employed facilitation additives during the bake of the first layer is compared to the performance of devices formed without facilitation additives where the first layer is baked at the same conditions (temperature and time) or at the champion bake conditions (typically a higher temperature). Effectiveness of the facilitation additive is determined by how much the performance of the test device using facilitation additives exceeds that of the devices baked at the same conditions without facilitation additives. For some facilitation additives the test device performance will even match (or exceed) that of the champion devices.

In some embodiments the layer which employs facilitation additives is a hole transport layer (HTL) and the subsequent layer is a light emissive layer (EML).

In some embodiments, the facilitation additive is deuterated. In some embodiments, the facilitation additive is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments, the facilitation additive is an aliphatic or deuterated aliphatic compound.

In some embodiments, the facilitation additive is a straight chain alkane having 10-50 carbons, or a deuterated analog thereof.

In some embodiments, the facilitation additive is a branched chain alkane having 10-50 carbons, or a deuterated analog thereof.

In some embodiments, the facilitation additive is an aromatic compound or deuterated aromatic compound.

In some embodiments, the facilitation additive has Formula VIII

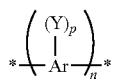

wherein:
Ar is the same or different at each occurrence and is an aryl group or deuterated aryl group having 3-60 ring carbons;
Y is the same or different at each occurrence and is selected from the group consisting of D, alkyl, alkoxy, aryl, aryloxy, carboxylic ester, silyl, siloxane, amino, carbazolyl, deuterated alkyl, deuterated alkoxy, deuterated aryl, deuterated aryloxy, deuterated carboxylic ester, deuterated silyl, deuterated siloxane, deuterated amino, and deuterated carbazolyl, where Y groups on adjacent carbons may be joined together to form a fused 5- or 6-membered aliphatic ring;
n is an integer greater than 0;
p is an integer greater than 0; and
* represents a point of attachment, H, D, halide, aryl, or deuterated aryl.

In some embodiments of Formula VIII, Ar is an aromatic group having no heteroatoms. In some embodiments, Ar has 6-30 ring carbons. In some embodiments, Ar is selected from the group consisting of phenyl, naphthyl, anthracenyl, phenanthrenyl, substituted derivatives thereof, and deuterated analogs thereof.

In some embodiments of Formula VIII, Ar is substituted with one or more groups selected from the group consisting of alkyl, alkoxy, silyl, silyl ether, arylamino, and deuterated analogs thereof.

In some embodiments of Formula VIII, Ar is a heteroaromatic group. In some embodiments, Ar is a heteroaromatic group having 3-20 ring carbons.

In some embodiments of Formula VIII, Ar is a heteroaromatic group having at least one nitrogen heteroatom. In some embodiments, Ar is selected from the group consisting of pyrrole, pyridine, triazine, quinoxaline, benzimidazole, carbazole, indolocarbazole, substituted derivatives, and deuterated analogs thereof.

In some embodiments of Formula VIII, Ar is a heteroaromatic group having at least one sulfur heteroatom. In some embodiments, Ar is selected from the group consisting of thiophene, benzothiophene, dibenzothiophene, thieneothiophene, substituted derivatives, and deuterated analogs thereof.

In some embodiments of Formula VIII, Ar is a heteroaromatic group having at least one oxygen heteroatom. In some embodiments, Ar is selected from the group consisting of furan, benzofuran, dibenzofuran, pyran, benzopyran, dibenzopyran, substituted derivatives thereof, and deuterated analogs thereof.

In some embodiments of Formula VIII, Ar is a heteroaromatic group having two or more different heteroatoms selected from N, O, and S. In some embodiments, Ar is selected from the group consisting of oxazole, oxazine, phenoxazine, thiazole, thiazine, substituted derivatives thereof, and deuterated analogs thereof.

In some embodiments of Formula VIII, Y is selected from the group consisting of D, alkyl, aryl, silyl, deuterated alkyl, deuterated aryl, and deuterated silyl.

In some embodiments of Formula VIII, Y is selected from from the group consisting of D, aryl, and deuterated aryl.

The aryl or deuterated aryl may have one or more substituents selected from the group consisting of alkyl, silyl, and deuterated analogs thereof.

In some embodiments of Formula VIII, there is at least one aryl amino group, carbazolyl group, or deuterated analog thereof.

In some embodiments of Formula VIII, there are no amino or carbazolyl groups.

In some embodiments of Formula VIII, n is 1 or 2.

In some embodiments, the facilitation additive has Formula IX

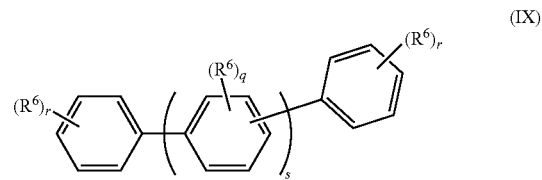

wherein:
$R^6$ is the same or different at each occurrence and is selected from the group consisting of D, alkyl, alkoxy, aryl, aryloxy, silyl, siloxane, amino, carbazolyl, deuterated alkyl, deuterated alkoxy, deuterated aryl, deuterated aryloxy, deuterated silyl, deuterated siloxane, deuterated amino, and deuterated carbazolyl, where $R^6$ groups on adjacent carbons may be joined together to form a fused 5- or 6-membered aliphatic ring;
q is the same or different at each occurrence and is an integer from 0-4;
r is the same or different at each occurrence and is an integer from 0-5; and
s is an integer from 0 to 5.

In some embodiments of Formula IX, $R^6$ is selected from the group consisting of D, alkyl, aryl, silyl, deuterated alkyl, deuterated aryl, and deuterated silyl.

In some embodiments of Formula IX, $R^6$ is selected from from the group consisting of D, alkyl, silyl, deuterated alkyl, and deuterated silyl.

In some embodiments of Formula IX, there is at least one aryl amino group.

In some embodiments of Formula IX, there are no amino or carbazolyl groups.

In some embodiments, the facilitation additive has Formula IX-a

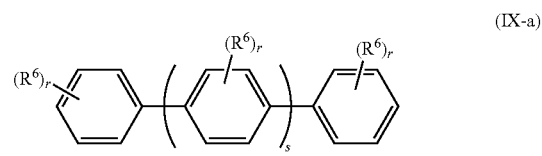

wherein $R^6$, q, r, and s are as defined above for Formula IX.

In some embodiments of Formula IX-a, $R^6$ is selected from the group consisting of D, alkyl, aryl, silyl, deuterated alkyl, deuterated aryl, and deuterated silyl.

In some embodiments of Formula IX-a, $R^6$ is selected from the group consisting of D, alkyl, silyl, deuterated alkyl, and deuterated silyl.

In some embodiments of Formula IX-a, there is at least one aryl amino group.

In some embodiments of Formula IX-a, there are no amino or carbazolyl groups.

In some embodiments, the facilitation additive is an aliphatic compound and has no aromatic rings.

In some embodiments, the facilitation additive is a branched or straight chain alkane or deuterated analog thereof having 5-75 carbons, which may be substituted or unsubstituted. In some embodiments, the alkane has 10-60 carbons; in some embodiments, 15-40 carbons.

In some embodiments, the facilitation additive is a substituted alkane. In some embodiments, the substituents are selected from the group consisting of D, halide, CN, OH, alkoxy, silyl, silyl ether, deuterated alkoxy, deuterated silyl, and deuterated silyl ether.

In some embodiments, the facilitation additive is a mixture of alkanes having 10-60 carbons or deuterated analogs thereof.

In some embodiments, the facilitation additive is an aliphatic hydrocarbon having one or more unsaturated bonds.

In some embodiments, the facilitation additive is an alkene having 10-60 carbons and one or more double bonds, or a deuterated analog thereof.

In some embodiments, the facilitation additive is a substituted alkene. In some embodiments, the substituents are selected from the group consisting of D, halide, CN, OH, alkoxy, silyl, silyl ether, deuterated alkoxy, deuterated silyl, and deuterated silyl ether.

In some embodiments, the facilitation additive is an alkyne having 10-60 carbons and one or more triple bonds, or a deuterated analog thereof.

In some embodiments, the facilitation additive is a substituted alkyne. In some embodiments, the substituents are selected from the group consisting of D, halide, CN, OH, alkoxy, silyl, silyl ether, deuterated alkoxy, deuterated silyl, and deuterated silyl ether.

In some embodiments, the facilitation additive is a polyalkylene oxide oligomer, or deuterated analog thereof.

Any of the above embodiments of the facilitation additive can be combined with one or more of the other embodiments, so long as they are not mutually exclusive. For example, the embodiment in which the facilitation additive is deuterated can be combined with the embodiment in which the facilitation additive is an aliphatic compound. The same is true for the other non-mutually-exclusive embodiments discussed above. The skilled person would understand which embodiments were mutually exclusive and would thus readily be able to determine the combinations of embodiments that are contemplated for the facilitation additive in the present application.

Some examples of facilitation additives include, but are not limited to heptadecane, hexatriacontane, mineral oil, anisole, methyl benzoate,

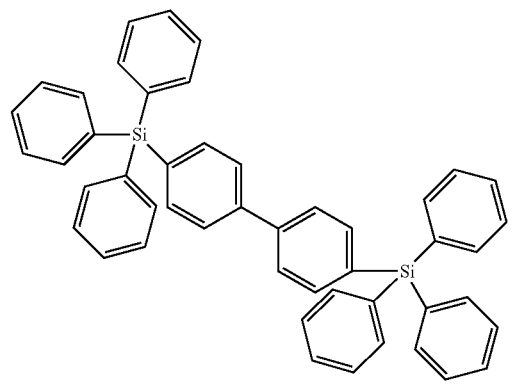

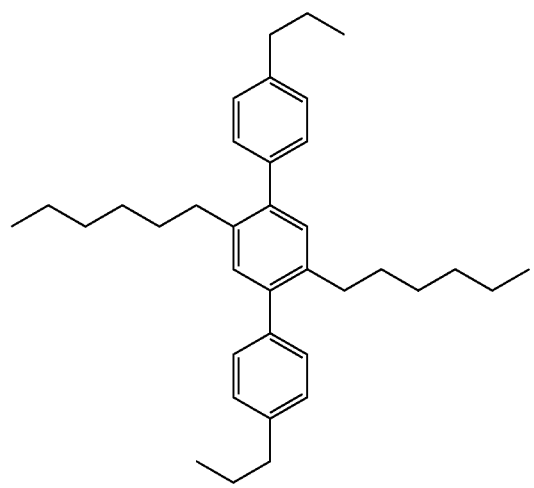

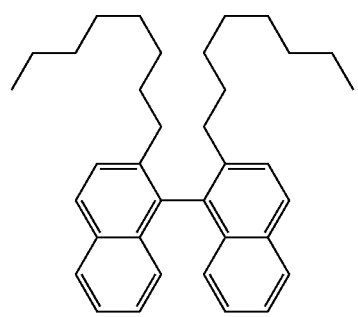

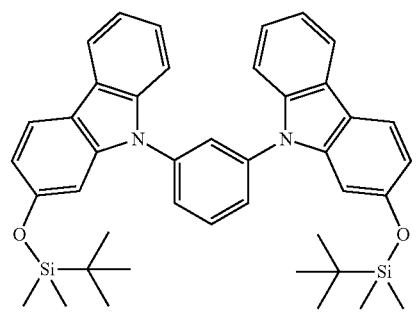

-continued

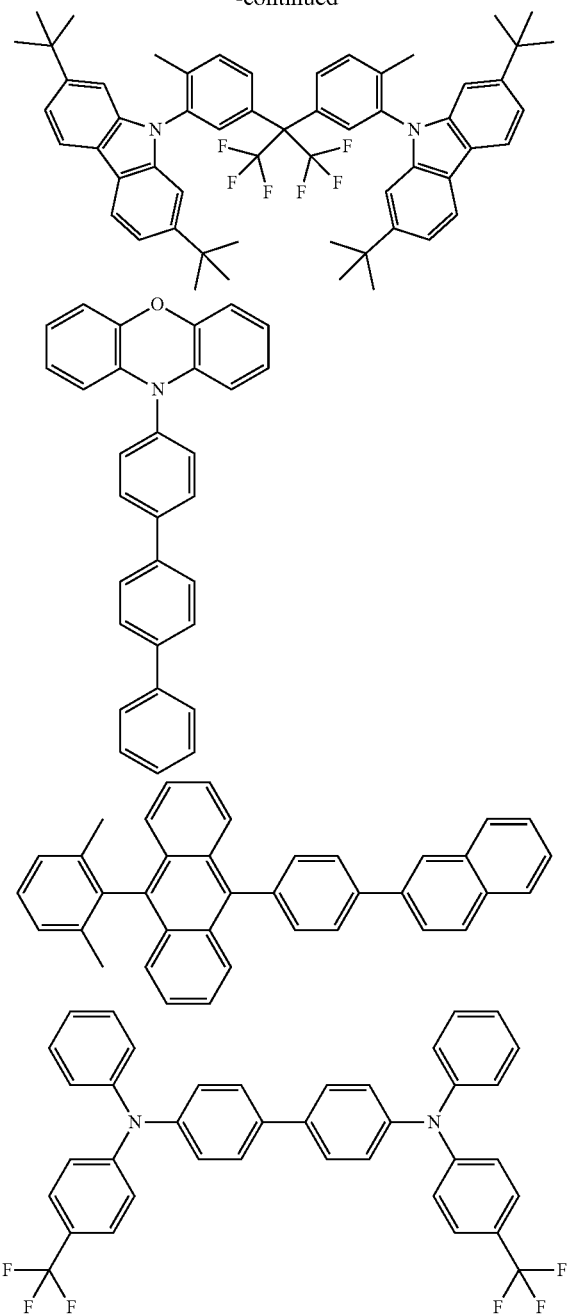

In general, the facilitation additive is commercially available or can be prepared using any technique that will yield a C—C or C—N bond. A variety of such techniques are known, such as Suzuki, Yamamoto, Stille, and Pd- or Ni-catalyzed C—N couplings.

The deuterated analog compounds can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum chloride, or acids such as $CF_3COOD$, DCl, etc. Deuteration reactions have also been described in published PCT application WO2011/053334.

(d) Liquid Medium

The liquid medium for the electroactive system is one in which the electroactive material can be dissolved or dispersed at the desired level, and from which a film can be formed. A suitable liquid medium for a particular electroactive material can be readily determined by one skilled in the art.

In some embodiments, the liquid medium is a polar non-aqueous solvent. Examples of polar solvents include, but are not limited to, $C_1$ to $C_{20}$ alcohols, ethers, and acid esters.

In some embodiments, the liquid medium is relatively non-polar solvent. Examples of non-polar solvents include, but are not limited to $C_1$ to $C_{12}$ alkanes, aromatics such as toluene, xylenes, trifluorotoluene, and the like.

In some embodiments, the liquid medium is a mixture of two or more solvents.

In some embodiments, the liquid medium is selected from the group consisting of a chlorinated hydrocarbon (such as methylene chloride, chloroform, chlorobenzene), an aromatic hydrocarbon (such as a substituted or non-substituted toluene or xylene, including trifluorotoluene), a polar solvent (such as tetrahydrofuran (THF), N-methyl pyrrolidone (NMP)), an ester (such as ethylacetate, methylbenzoate, or diethylphthalate), an ether (such as anisole or dimethoxybenzene), an alcohol (such as isopropanol), a ketone (such as cyclopentanone), and any mixture thereof.

Suitable solvents for electroluminescent materials have been described in, for example, published PCT application WO 2007/145979.

4. Process (a) Process 1

In some embodiments, the process includes the steps:
  (i) depositing a first electroactive composition onto a workpiece, to form a deposited layer, wherein the first electroactive composition includes a first electroactive material, a facilitation additive, and a first liquid medium;
  (ii) baking the deposited layer at a temperature less than 350° C. for a predetermined time; and
  (iii) depositing over the first electroactive layer a second electroactive composition comprising a second electroactive material in a second liquid medium;

wherein the facilitation additive is present in an amount sufficient to enable the first electroactive layer to effectively resist mixing with the second liquid medium.

In some embodiments, the first electroactive composition includes only a first electroactive material, a facilitation additive, and a first liquid medium, where components that would materially alter the function, the principle of operation, or the distinguishing characteristics of the composition are not present.

In some embodiments, the first electroactive composition further includes additional materials which facilitate the function of the material.

In some embodiments, the first electroactive material includes a hole transport material, as discussed above.

In some embodiments, the first electroactive material includes a photoactive material, as discussed above.

In some embodiments, the first electroactive material includes at least one photoactive material and at least one host material, as discussed above.

In some embodiments, the weight ratio of the electroactive material to the facilitation additive in the first electroactive composition is in the range of 19:1 to 1:1; in some embodiments, 10:1 to 1.5:1.

In some embodiments of the first electroactive composition, the total solids is in the range of 1-10% by weight; in some embodiments, 2-5% by weight.

In some embodiments, the workpiece includes a substrate having an electrode thereon. In some embodiments, the electrode is an anode.

In some embodiments, the workpiece includes a substrate having thereon an electrode and one or more organic electroactive layers.

In some embodiments, the workpiece includes a TFT backplane, including electronic components, circuits, and/or conductive members.

In some embodiments, the workpiece includes a TFT backplane and one or more organic electroactive layers thereon.

The first electroactive composition is deposited onto the workpiece by any liquid deposition method to form a deposited layer. Liquid deposition techniques include, but are not limited to, spin coating, gravure coating, curtain coating, dip coating, slot-die coating, spray coating, continuous nozzle coating, ink jet printing, gravure printing, and screen printing.

In some embodiments, the first electroactive composition is deposited by continuous nozzle coating or ink jet printing.

The deposited layer is then baked to form a first electroactive layer.

The deposited layer is baked at a temperature less than 350° C. In some embodiments, the baking temperature is less than or equal to 325° C.; in some embodiments, less than or equal to 300° C.; in some embodiments, less than or equal to 275° C.; in some embodiments, less than or equal to 250° C.; in some embodiments, less than or equal to 225° C.; in some embodiments, less than or equal to 200° C.; in some embodiments, less than or equal to 175° C. In general, the baking temperature is at least 100° C.

In some embodiments, the baking step includes two or more different baking stages at different temperatures. When two or more baking stages are used, the highest baking temperature is less than 350° C. In some embodiments, the highest baking temperature is less than or equal to 325° C.; in some embodiments, less than or equal to 300° C.; in some embodiments, less than or equal to 275° C.; in some embodiments, less than or equal to 250° C.; in some embodiments, less than or equal to 225° C.; in some embodiments, less than or equal to 200° C.; in some embodiments, less than or equal to 175° C. In general, the highest baking temperature is at least 100° C.

In some embodiments, the deposited layer is enclosed with a complete or partial enclosure for the baking step. This enclosure increases the local vapor pressure of the additive, thereby reducing the rate at which it leaves the electroactive layer. This can be accomplished, for example, by placing a glass lid over the deposited layer during the baking step. Any material can be used for the enclosure as long as it does not interact with or deleteriously affect the electroactive material.

In some embodiments, the baking step is carried out at atmospheric pressure.

In some embodiments, the baking step is carried out at pressures less than atmospheric pressure. In some embodiments, the pressure is less than 90 kPa; in some embodiments, less than 50 kPa. In general, the pressure is at least 1 kPa.

The predetermined baking time for the deposited layer depends on the baking temperature. When two or more baking stages are used, as discussed above, there will be a predetermined baking time for each stage. The total predetermined baking time is the sum of the baking times for each stage.

In some embodiments, the baking time is the time required to remove substantially all of the first liquid medium at the baking temperature selected. By removing "substantially all" it is meant that no detectable liquid medium remains in the deposited layer. In some embodiments, the predetermined time is 30 minutes or less; in some embodiments, 20 minutes or less; in some embodiments, 10 minutes or less. In general, the baking time is at least 5 minutes.

In some embodiments, the facilitation additive remains present in the first electroactive layer.

In some embodiments, the facilitation additive is at least partially removed in the baking step and only partially remains in the first electroactive layer.

In some embodiments, the facilitation additive is essentially completely removed in the baking step. In some embodiments, there is no detectable level of facilitation additive in the first electroactive layer.

A second electroactive composition is then deposited over the thus-formed first electroactive layer. The second electroactive composition includes a second electroactive material in a second liquid medium.

The second electroactive material can be a single compound or a combination of two or more compounds.

In some embodiments, the second electroactive material includes a hole transport material, as discussed above.

In some embodiments, the second electroactive material includes a photoactive material, as discussed above.

In some embodiments, the second electroactive material includes at least one photoactive material and at least one host material, as discussed above.

In some embodiments, the second electroactive material includes electron transport material, as discussed below.

The second liquid medium is one in which the second electroactive material can be dissolved or dispersed at the desired level, and from which a film can be formed. A suitable liquid medium for a particular electroactive material can be readily determined by one skilled in the art. Exemplary liquid media are discussed above.

In some embodiments, the second liquid medium is selected from the group consisting of a chlorinated hydrocarbon (such as methylene chloride, chloroform, chlorobenzene), an aromatic hydrocarbon (such as a substituted or non-substituted toluene or xylene, including trifluorotoluene), a polar solvent (such as tetrahydrofuran (THF), N-methyl pyrrolidone (NMP)), an ester (such as ethylacetate, methylbenzoate, or diethylphthalate), an ether (such as anisole or dimethoxybenzene), an alcohol (such as isopropanol), a ketone (such as cyclopentanone), and any mixture thereof.

The first electroactive layer formed in the above process is effectively resistant to mixing with the second liquid medium. By this it is meant that there is substantially no mixing of the deposited electroactive material into the bulk of the hole transport layer. In some embodiments, this means that the materials and conditions result in passing the PLT, as described above. In some embodiments, this means that the materials and conditions result in passing the SCOLEDT, as described above. In some embodiments, this means that the materials and conditions result in passing the NPOLEDT, as described above. In some embodiments, this means that the materials and conditions result in passing the IJPOLEDT, as described above.

In some embodiments, the first electroactive material includes a first hole transport material and the second electroactive material includes a second hole transport material.

In some embodiments, the first electroactive material includes hole transport material and the second electroactive material includes photoactive material.

In some embodiments, the first electroactive material includes photoactive material and the second electroactive material includes electron transport material.

(b) Process 2

In some embodiments, the process includes the steps:
(i) depositing a first electroactive composition onto a workpiece to form a deposited layer, wherein the first electroactive composition includes a first electroactive material and a first liquid medium;
(ii) baking the deposited layer in the presence of a facilitation additive, where the baking is carried out at a temperature less than 350° C. for a predetermined time; and
(iii) depositing over the first electroactive layer a second electroactive composition comprising a second electroactive material in a second liquid medium;
wherein the facilitation additive is present in an amount sufficient to enable the first electroactive layer to effectively resist mixing with the second liquid medium.

In some embodiments, the first electroactive composition includes only a first electroactive material and a first liquid medium, where components that would materially alter the function, the principle of operation, or the distinguishing characteristics of the composition are not present.

In some embodiments, the first electroactive composition further includes additional materials which facilitate the function of the material.

In some embodiments, the first electroactive material includes a hole transport material, as discussed above.

In some embodiments, the first electroactive material includes a photoactive material, as discussed above.

In some embodiments, the first electroactive material includes at least one photoactive material and at least one host material, as discussed above.

In some embodiments of the first electroactive composition, the total solids is in the range of 1-10% by weight; in some embodiments, 2-5% by weight.

The workpiece are as described above for Process 1.

The first electroactive composition is deposited onto the workpiece by any liquid deposition method to form a deposited layer.

In some embodiments, the first electroactive composition is deposited by continuous nozzle coating or ink jet printing.

The deposited layer is then baked in the presence of a facilitation additive to form a first electroactive layer. By this it is meant that the facilitation additive is in close proximity to the deposited layer.

In some embodiments, the facilitation additive is present in the form of a layer on a separate inert substrate that is positioned over the deposited layer during the baking step. In some embodiments, the inert substrate is glass. In some embodiments, the inert substrate is a plastic that is unaffected by the baking temperature.

In some embodiments, the facilitation additive is present as a coating in a cavity of an inert substrate. The substrate forms a type of lid which is placed over the deposited layer during the baking step, with the coated cavity facing the deposited layer.

In some embodiments, the facilitation additive is present as a vapor in an enclosed or partially enclosed baking apparatus.

In some embodiments, the facilitation additive is present as a separate layer deposited over the deposited layer of first electroactive material prior to the baking step. The facilitation additive can be deposited from any liquid medium in which it can be dissolved or dispersed and from which a layer can be formed. The layer can be formed by a liquid deposition method.

The facilitation additive is generally present in substantial excess relative to the first electroactive material.

The deposited layer is then baked in the presence of the facilitation additive at a temperature less than 350° C. In some embodiments, the baking temperature is less than or equal to 325° C.; in some embodiments, less than or equal to 300° C.; in some embodiments, less than or equal to 275° C.; in some embodiments, less than or equal to 250° C.; in some embodiments, less than or equal to 225° C.; in some embodiments, less than or equal to 200° C.; in some embodiments, less than or equal to 175° C. In general, the baking temperature is at least 100° C.

In some embodiments, the baking step includes two or more different baking stages at different temperatures. When two or more baking stages are used, the highest baking temperature is less than 350° C. In some embodiments, the highest baking temperature is less than or equal to 325° C.; in some embodiments, less than or equal to 300° C.; in some embodiments, less than or equal to 275° C.; in some embodiments, less than or equal to 250° C.; in some embodiments, less than or equal to 225° C.; in some embodiments, less than or equal to 200° C.; in some embodiments, less than or equal to 175° C. In general, the highest baking temperature is at least 100° C.

In some embodiments, the baking step is carried out at atmospheric pressure.

In some embodiments, the baking step is carried out at pressures less than atmospheric pressure. In some embodiments, the pressure is less than 90 kPa; in some embodiments, less than 50 kPa. In general, the pressure is at least 1 kPa.

The predetermined baking time for the deposited layer depends on the baking temperature. When two or more baking stages are used, as discussed above, there will be a predetermined baking time for each stage. The total predetermined baking time is the sum of the baking times for each stage.

In some embodiments, the baking time is the time required to remove substantially all of the first liquid medium at the baking temperature selected. By removing "substantially all" it is meant that no detectable liquid medium remains in the deposited layer. In some embodiments, the total predetermined time is 30 minutes or less; in some embodiments, 20 minutes or less; in some embodiments, 10 minutes or less. In general, the baking time is at least 5 minutes.

In some embodiments, some facilitation additive remains over the first electroactive layer.

In some embodiments, some facilitation additive diffuses into the first electroactive layer and remains in that layer.

In some embodiments, there is no facilitation additive remaining over or in the first electroactive layer after the baking step. In some embodiments, there is no detectable level of facilitation additive in the first electroactive layer.

A second electroactive composition is then deposited over the thus-formed first electroactive layer. The second electroactive composition includes a second electroactive material in a second liquid medium.

The second electroactive material can be a single compound or a combination of two or more compounds.

In some embodiments, the second electroactive material includes a hole transport material, as discussed above.

In some embodiments, the second electroactive material includes a photoactive material, as discussed above.

In some embodiments, the second electroactive material includes at least one photoactive material and at least one host material, as discussed above.

In some embodiments, the second electroactive material includes electron transport material, as discussed below.

The second liquid medium is one in which the second electroactive material can be dissolved or dispersed at the desired level, and from which a film can be formed. A suitable liquid medium for a particular electroactive material can be readily determined by one skilled in the art. Exemplary liquid media are discussed above.

The first electroactive layer formed in the above process is effectively resistant to mixing with the second liquid medium. By this it is meant that there is substantially no mixing at the interface between the hole transport layer and the deposited electroactive material. In some embodiments, this means that the materials and conditions result in passing the PLT, as described above.

In some embodiments, the first electroactive material includes a first hole transport material and the second electroactive material includes a second hole transport material.

In some embodiments, the first electroactive material includes hole transport material and the second electroactive material includes photoactive material.

In some embodiments, the first electroactive material includes photoactive material and the second electroactive material includes electron transport material.

3. Electronic Devices

Organic electronic devices that may benefit from the hole transport system as described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), and (4) devices that include one or more electronic components that include one or more organic semi-conductor layers (e.g., a transistor or diode).

Figure 4:
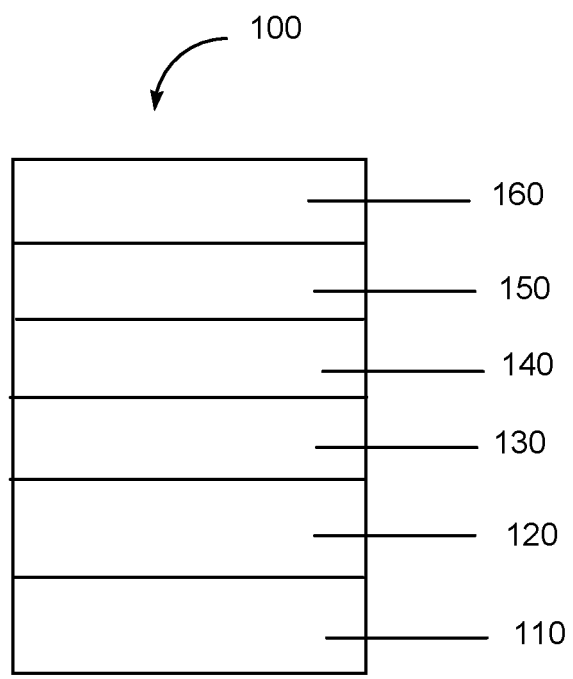
FIG. 4 includes an illustration of one example of an organic electronic device.

One illustration of an organic electronic device structure is shown in FIG. 4. The device 100 has a first electrical contact layer, an anode layer 110 and a second electrical contact layer, a cathode layer 160, and a photoactive layer 140 between them. Additional layers may optionally be present. Adjacent to the anode may be a hole injection layer 120, sometimes referred to as a buffer layer. Adjacent to the hole injection layer may be a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160. Layers 120 through 150 are individually and collectively referred to as the active layers.

Figure 5:
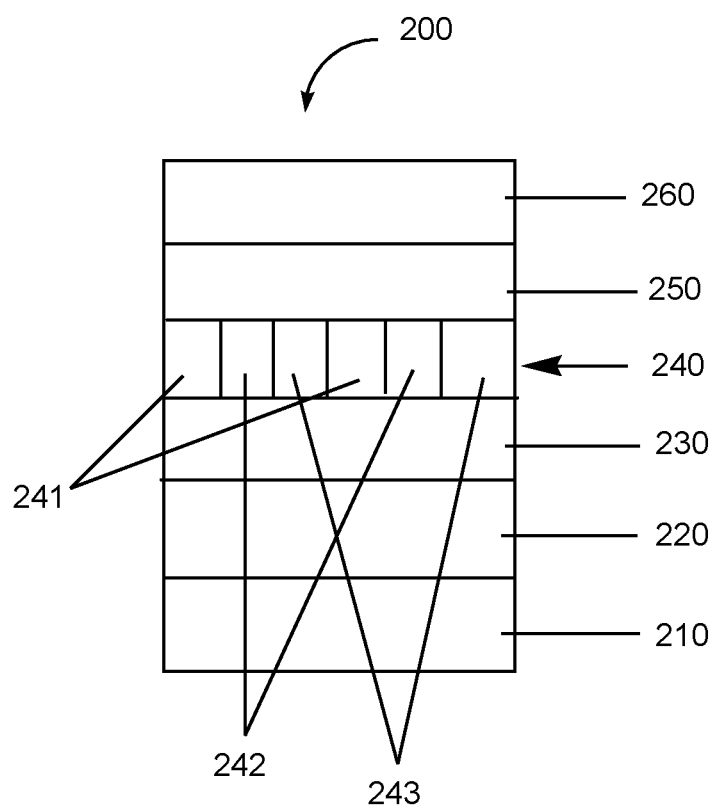
FIG. 5 includes another illustration of an organic electronic device.

In some embodiments, in order to achieve full color, the light-emitting layer is pixellated, with subpixel units for each of the different colors. An illustration of a pixellated device is shown in FIG. 5. The device 200 has anode 210, hole injection layer 220, hole transport layer 230, photoactive layer 240, electron transport layer 250, and cathode 260. The electroluminescent layer is divided into subpixels 241, 242, 243, which are repeated across the layer. In some embodiments, the subpixels represent red, blue and green color emission. Although three different subpixel units are depicted in FIG. 5, two or more than three subpixel units may be used.

The different layers will be discussed further herein with reference to FIG. 4. However, the discussion applies to FIG. 5 and other configurations as well.

In some embodiments, the different layers have the following range of thicknesses: anode 110, 500-5000 Å, in one embodiment 1000-2000 Å; hole injection layer 120, 50-2000 Å, in one embodiment 200-1000 Å; hole transport layer 130, 50-2000 Å, in one embodiment 200-1000 Å; photoactive layer 140, 10-2000 Å, in one embodiment 100-1000 Å; electron transport layer 150, 50-2000 Å, in one embodiment 100-1000 Å; cathode 160, 200-10000 Å, in one embodiment 300-5000 Å. The desired ratio of layer thicknesses will depend on the exact nature of the materials used.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide ("ITO"), are generally used. The anode may also comprise an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

Optional hole injection layer 120 includes hole injection materials. The term "hole injection layer" or "hole injection material" is intended to mean electrically conductive or semiconductive materials and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules, and may be in the form of solutions, dispersions, suspensions, emulsions, colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like. The hole injection layer 120 can comprise charge transfer compounds, and the like, such as copper phthalocyanine and the tetrathiafulvalene-tetracyanoquinodimethane system (TTF-TCNQ). In some embodiments, the hole injection layer 120 is made from a dispersion of a conducting polymer and a colloid-forming polymeric acid. Such materials have been described in, for example, published U.S. patent applications 2004-0102577, 2004-0127637, and 2005-0205860.

Layer 130 includes hole transport material. Suitable hole transport materials have been discussed above.

In some embodiments, the hole transport layer is the first electroactive layer made, according to Process 1.

In some embodiments, the hole transport layer is the first electroactive layer made, according to Process 2.

Depending upon the application of the device, the photoactive layer 140 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Suitable photoactive materials have been discussed above.

In some embodiments, photoactive layer 140 includes an electroluminescent material and one or more host materials, as discussed above.

Optional layer 150 can function both to facilitate electron transport, and also serve as an electron injection layer or confinement layer to prevent quenching of the exciton at layer interfaces. Preferably, this layer promotes electron mobility and reduces exciton quenching. Examples of electron transport materials which can be used in the optional electron transport layer 150, include metal chelated oxinoid compounds, including metal quinolate derivatives such as tris(8-hydroxyquinolato)aluminum (AlQ), bis(2-methyl-8-quinolinolato)(p-phenylphenolato)aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyI)-4-phenyl-5-(4-t-butylphenyl)-1,2,4-triazole (TAZ), and 1,3,5-tri(phenyl-2-benzimidazole) benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); triazines; fullerenes; and mixtures thereof. In some embodiments, the electron transport material is selected from the group consisting of metal quinolates and phenanthroline derivatives. In some embodiments, the electron transport layer further includes an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, $Li_2O$, Cs-containing organometallic compounds, CsF, $Cs_2O$, and $Cs_2CO_3$ can also be deposited between the organic layer and the cathode layer to lower the operating voltage. This layer may be referred to as an electron injection layer.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

In some embodiments, each functional layer 110-160, is a single layer.

The device layers can be formed by any deposition technique, or combinations of techniques, including vapor deposition, liquid deposition, and thermal transfer. Substrates such as glass, plastics, and metals can be used. Conventional vapor deposition techniques can be used, such as thermal evaporation, chemical vapor deposition, and the like. The organic layers can be applied from solutions or dispersions in suitable solvents, using conventional coating or printing techniques, including but not limited to spin-coating, dip-coating, roll-to-roll techniques, ink-jet printing, continuous nozzle printing, screen-printing, gravure printing and the like.

In some embodiments, the device has the following structure, in order: anode, hole injection layer, hole transport layer, electroactive layer, electron transport layer, electron injection layer, cathode.

Although methods and materials similar or equivalent to those described herein can be used in the practice or testing of the present invention, suitable methods and materials are described below. In addition, the materials, methods, and examples are illustrative only and not intended to be limiting.

EXAMPLES

The concepts described herein will be further described in the following examples, which do not limit the scope of the invention described in the claims.

Synthesis Example 1

This example illustrates the synthesis of hole transport material HT-1, shown below.

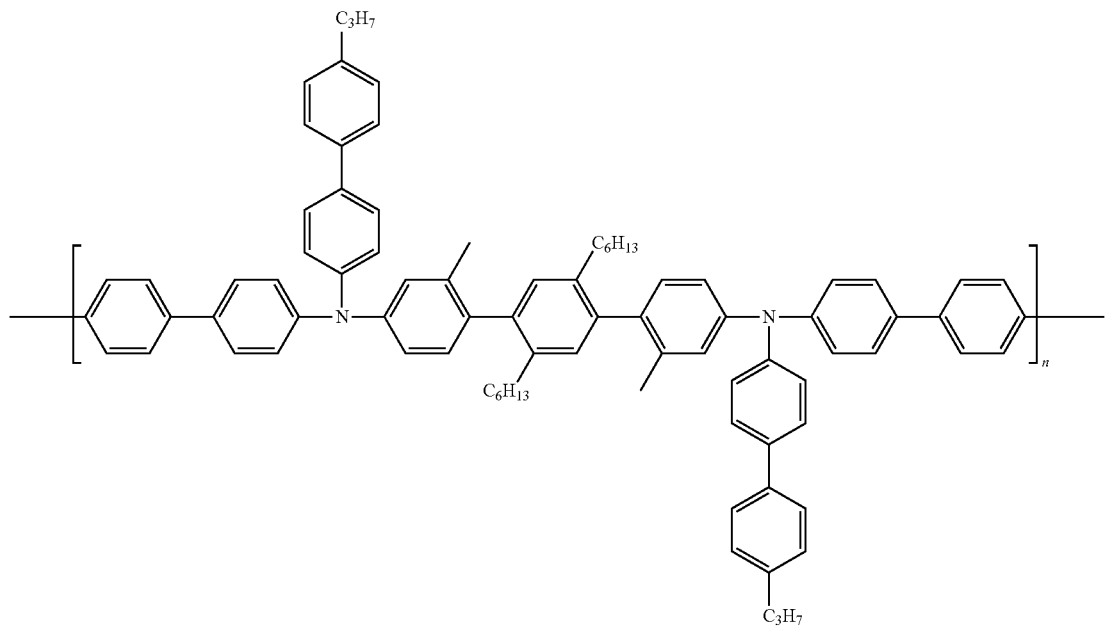

Step 1:

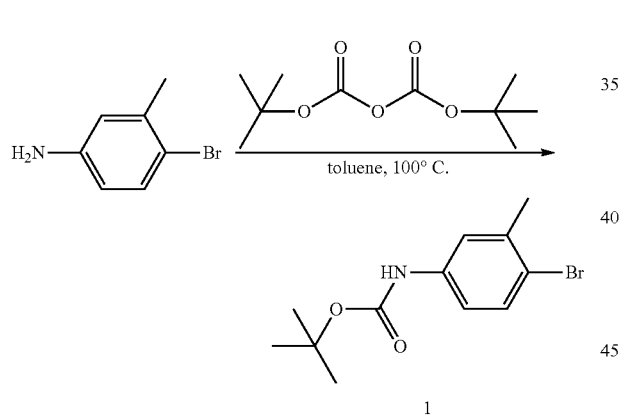

The reaction mixture of 4-bromo-3-methylaniline (11 g, 59.12 mmol) and (Boc)$_2$O (12.9 g, 59.12 mmol) in toluene (110 ml) was stirred at 100° C. for 40 h under nitrogen. After concentration of the reaction mixture under reduced pressure, 15.9 g (94% yield) of boc-NH-4-bromo-3-methylaniline, 1, was obtained as a white solid by column chromatography (5-10% ethyl acetate in hexane).

Step 2:

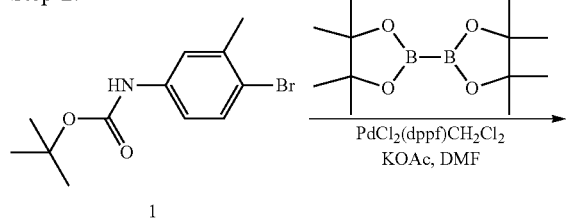

-continued

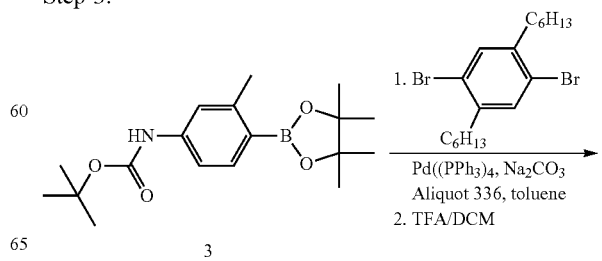

In a glove box a mixture of the boc-NH-4-bromo-3-methylaniline, 1, (20.77 g, 72.58 mmol), diboron pinacol ester (22.12 g, 87.09 mmol), 1,1'-bis-(diphenylphosphino)ferrocine palladium dichloride (1.43 g, 1.96 mmol), and potassium acetate (21.37 g, 217.7 mmol) in dry degassed DMF (300 mL) was stirred at 80° C. for 16 hrs in an oil bath. The mixture was cooled to room temperature and concentrated under reduced pressure. DCM (100 mL) was added to the mixture which was filtered through a pad of Celite. The filtrate was concentrated to rusty oil which was purified on a silica gel column chromatography (5-10% EtOAc/hexane) to provide the product, 3, (18.57 g, 77% yield) as a white solid.

Step 3:

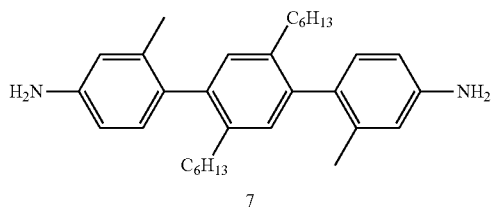

In the dry box the mixture of boronic acid pinacol ester,3, (5.6 g, 16.82 mmol), 1,4-dibromo-2,5-dihexylbenzene (3.4 g, 8.4 mmol), Aliquat 336 (0.8 g), and Pd(PPh₃)₄ (0.486 g, 0.421 mmol) in degassed toluene (100 mL) was prepared. Outside dry box, the degassed Na₂CO₃ (2.67 g, 25.23 mmol in 50 mL of water) solution was added to the former mixture under nitrogen, and then the resultant mixture was stirred at 90° C. for 42 hrs. The organic layer was separated and the aqueous layer was extracted with ethyl acetate. The combined organic layers were dried over anhydrous MgSO₄. Filtration, concentration of the filtrate, and then the silica column chromatography (0-3% ethyl acetae in hexane) provided the desired product (2.11 g, 38% yield) as a viscous liquid. This diboc-protected material was deprotected by the overnight reaction at room temperature with TFA solution (5 mL of TFA in 50 mL of DCM). Concentration of the reaction mixture followed by the neutralization with saturated NaHCO₃, then silica column chromatography (30% ethylacetae in hexane) provided the desired diamine material,7, (1.16 g, 80% yield) as a viscous liquid.

Step 4:

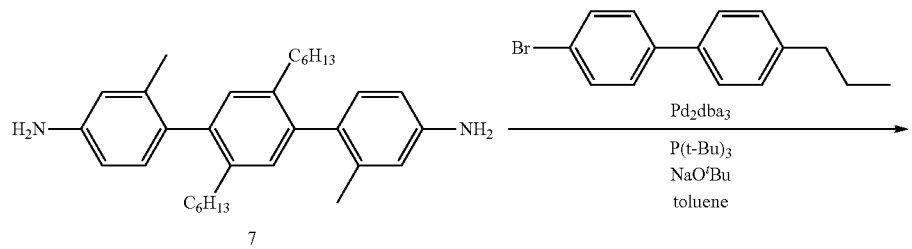

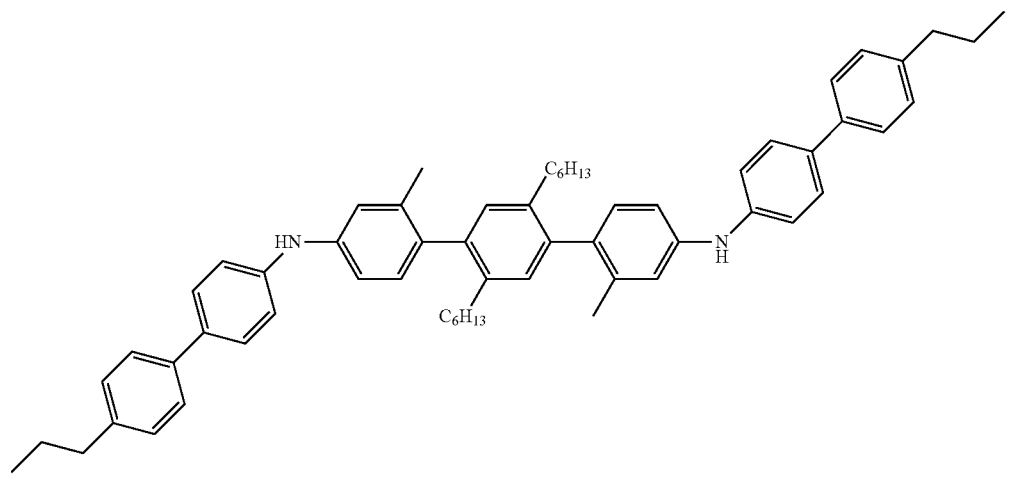

To the solution of diamine, 7, (1.06 g, 2.32 mmol) and 4-bromo-4'-propyl-biphenyl (1.28 g, 4.65 mmol) in toluene (20 mL) was added the solution of pd$_2$dba$_3$ (128 mg, 0.139 mmol) and P(t-Bu)$_3$ (57 mg, 0.278 mmol) in toluene (10 mL), followed by the addition of NaO$^t$Bu (0.45 g, 4.65 mmol) under nitrogen. The resultant mixture was stirred at room temperature overnight. The mixture was filtered through a short silica bed and the filtrate was concentrated under reduced pressure. By column chromatography (10-30% toluene in hexane) 1.35 g of product 10 was obtained as a solid (69% yield).

Step 5:

Step 6:

Compound M is polymerized to form polymer HT-1.

Compound M (0.50 mmol) is added to a scintillation vial and dissolved in 16 mL toluene. A clean, dry 50 mL Schlenk tube is charged with bis(1,5-cyclooctadiene)nickel(0) (1.010 mmol). 2,2'-Dipyridyl (1.010 mmol) and 1,5-cyclooctadiene (1.010 mmol) are weighed into a scintillation vial and are dissolved in 4 mL N,N'-dimethylformamide. The solution is added to the Schlenk tube. The Schlenk tube is heated to an internal temperature of 60° C. The catalyst system is held at

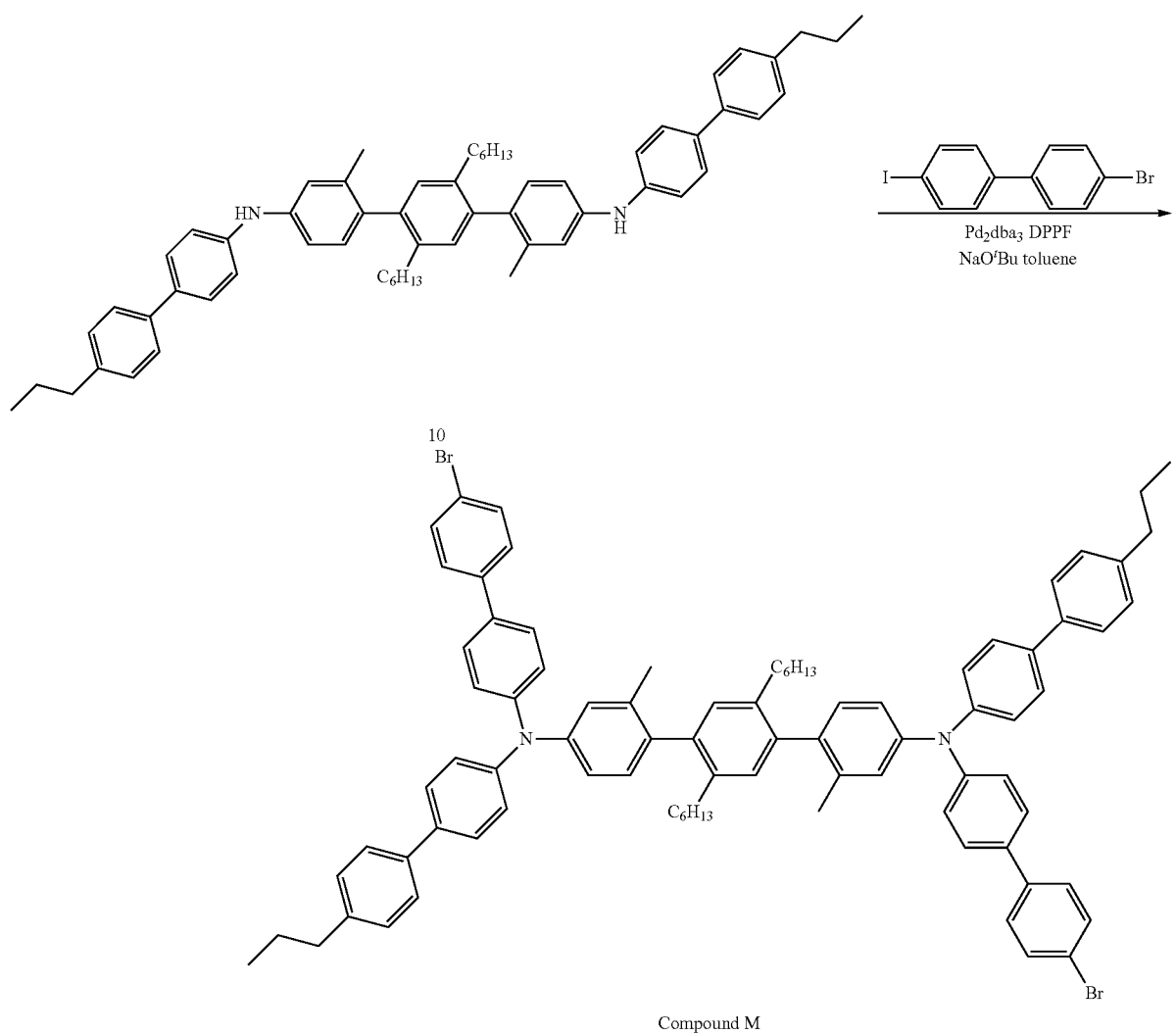

Compound M

To the solution of diamine, 10, (1.25 g, 1.48 mmol) and 4-bromo-4'-iodobiphenyl (1.59 g, 4.44 mmol) in toluene (30 mL) was added the solution of pd$_2$dba$_3$ (37 mg, 0.04 mmol) and DPPF (43 mg, 0.078 mmol) in toluene (10 mL), followed by the addition of NaO$^t$Bu (0.355 g, 3.70 mmol) under nitrogen. The resultant mixture was stirred at 95° C. for 16 hrs. The mixture was filtered through a short silica bed and the filtrate was concentrated under reduced pressure. By column chromatography (0-12% toluene in hexane) 1.10 g of product, Compound M, was obtained as a solid (57% yield).

60° C. for 30 minutes and then raised to 70° C. The monomer solution in toluene is added to the Schlenk tube and the tube is sealed. The polymerization mixture is stirred at 70° C. for 18 h. After cooling, the contents are poured into a solution of conc. HCl/MeOH (1.5% v/v conc. HCl). After stirring for 2 h, the polymer is collected by vacuum filtration and is dried under high vacuum. The polymer is purified by successive precipitations from toluene into HCl/MeOH (1% v/v conc. HCl), MeOH, toluene (CMOS grade), and ethyl acetate. NMR analysis confirms the structure of polymer HT-1.

Synthesis Example 2

This example illustrates the synthesis of photoactive material E-1, shown below.

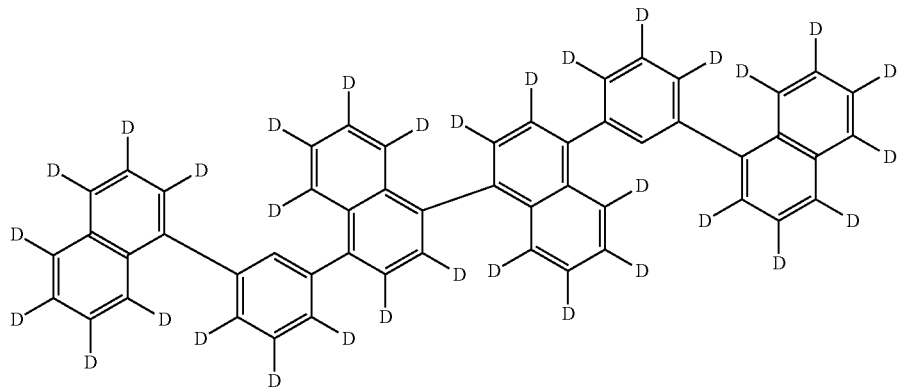 [SMILES: [2H]c1c(-c2c([2H])c([2H])c([2H])c3c([2H])c([2H])c([2H])c([2H])c23)cc(-c2c([2H])c([2H])c(-c3c([2H])c([2H])c(-c4cc(-c5c([2H])c([2H])c([2H])c6c([2H])c([2H])c([2H])c([2H])c56)c([2H])c([2H])c4[2H])c4c([2H])c([2H])c([2H])c([2H])c34)c3c([2H])c([2H])c([2H])c([2H])c23)c([2H])c1[2H]]

Step 1. 4,4'-bis(3-(naphthalen-1-yl)phenyl)-1,1'-binaphthalene

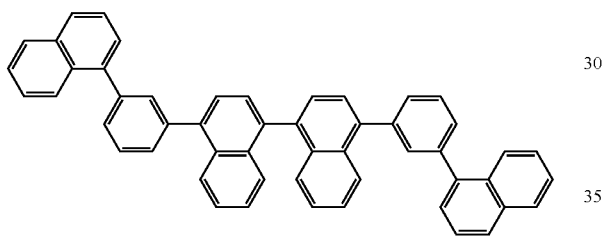

To a 500 mL round bottle flask were added 4,4'-dibromo-1,1'-binaphthyl (4.12 g, 10 mmol), 3-(naphthalen-1-yl)phenylboronic acid (5.21 g, mmol), sodium carbonate (2 M, 30 mL, 60 mmol), toluene (120 mL) and Aliquat 336 (0.5 g). The mixture was system was stirred under nitrogen for 20 min. After which Tetrakis(triphenylphospine) (462 mg, 0.4 mmol) was added and the mixture was stirred under nitrogen for another 15 min. The reaction was stirred and refluxed in an oil bath at 95° C. under nitrogen for 18 hour. After cooling to ambient temperature, some solid was seen formed and it was collected by filtration. The organic phase was separated, washed with water (60 mL), diluted HCl (10%, 60 mL) and saturated brine (60 mL) and dried with $MgSO_4$. The solution was filtered through a Silica gel plug and the solvent was removed by rotary evaporation. The solid collected earlier was triturated with hexane, filtered and combined with the residue from the liquid part. The material was redissolved in DCM/hexane and passed through a Silica gel column eluted with DCM/hexane. The product containing fractions were collected and the solvent was removed by rotary evaporation. The product was crystallized twice from toluene/EtOH to give the product as a white crystalline material. Yield, 2.60 g (39.52%). NMR spectrum was consistent with the structure.

Step 2

The deuterated compound E-1 was prepared by dissolving the above compound in d6-benzene and slowly adding d-triflic acid. The solution was stirred overnight in a drybox. The solution was then quenched with 10 st % sodium carbonate in D2O. The organic layer was separated, dried with magnesium sulfate, and purified by column chromatography, followed by precipitation.

Synthesis Example 3

This example illustrates the preparation of a facilitation additive, FA-1 shown below.

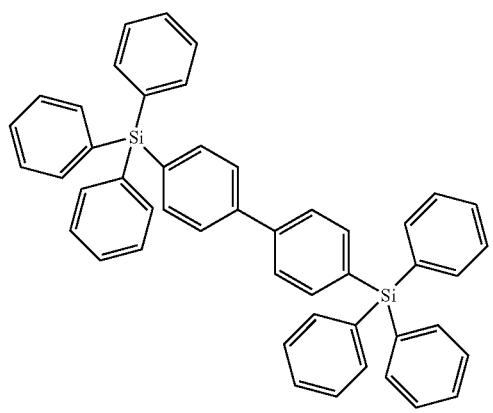 [SMILES: c1ccc([Si](c2ccccc2)(c2ccccc2)c2ccc(-c3ccc([Si](c4ccccc4)(c4ccccc4)c4ccccc4)cc3)cc2)cc1]

Anhydrous THF (150 ml) and 4,4'-dibromobiphenyl (10 g, 32.05 mmol) were placed into an oven-dried 500 mL three-neck round-bottom flask equipped with a magnetic stir bar and an addition funnel under $N_2$ atmosphere. Reaction mixture was cooled to −76° C. in a dry ice/acetone bath. n-BuLi (44 ml, 1.6 M solution in hexanes, 270.5 mmol) was charged to the addition funnel via cannula and added dropwise to the reaction mixture, maintaining the temperature at −74° C. to −76° C. The addition took 30 minutes. The addition funnel was rinsed with THF (10 ml) and the reaction was stirred at −74° C. for an hour longer, resulting in an off-white solution with white precipitate. Meanwhile, chlorotriphenylsilane (20.8 g, 70.5 mmol) was charged into an oven-dried 200 mL round-bottom flask and dissolved in 100 mL of dry THF under $N_2$ atmosphere. The silane solution was transferred to the addition funnel with a cannula. It was then added to the reaction mixture dropwise, over 90 min, at −74° C. After addition was complete, the addition funnel was washed with dry THF (10 mL). Reaction mixture was left to warm up to room temperature and stir overnight. A white precipitate was visible in the reaction flask next day. Methanol (10 ml) was added to the reaction mixture to quench any residual lithiated species. Volatiles were removed on the rotovap. The solid residue was taken up in diethyl ether (300 ml), ethyl acetate (100 ml) and water (200 ml). Organic phase was separated and washed two more times with water (200 ml each time). The organic layer was filled with solids. Collected solids suspended in the organic layer by vacuum filtration. Isolated solids were redissolved in 4 liters of dichloromethane and washed with water (3×1 L) and brine (1 L). Organic phase was dried over $MgSO_4$ and then concentrated to yield 18.5 g (86%) of a white solid. $^1H$ NMR was consistent with the target molecule.

Photoluminescence Test ("PLT")

As described above, the PLT is a test for the effectiveness of facilitation additives.

The materials used were hole transport material HT-1, with a weight average molecular weight of about 100,000 to 300,000, and photoactive material E-1.

Both HT-1 and E-1 can be excited by 300 nm light. The photoluminescence ("PL") spectrum for HT-1 is shown in FIG. 1A, as Material A. The PL spectrum for E-1 shown in FIG. 1B, as Material B. The PL spectrum for E-1 is at higher energy compared to the PL spectrum for HT-1.

Test coupons were made with a first layer of HT-1, with or without facilitation additives, overcoated by solution deposition of a second layer of E-1. The first layer was deposited by spin-coating a test solution of HT-1 onto a substrate of ITO/glass, to a thickness of 20 nm. The test solutions contained 0.44 wt. % HT-1 in toluene, with different levels of different facilitation additives. The control test solution had no facilitation additive. After spin coating, the deposited material was baked at various temperature for various times. After this, a solution of 4.0 wt. % E-1 in methyl benzoate was deposited by spin coating over the first layer to a thickness of 60 nm. The substrate was subsequently baked at 135° C. for 15 minutes on a hot plate. The composite of two layers was then encapsulated with a glass lid. The encapsulated composite of two layers was exposed to 300 nm light and the PL spectrum was obtained with in spectrofluorimeter Florolog-3 using front face geometry. If the first layer effectively resists mixing with the solvent for the second layer, there will be no more than a small amount of mixing of the layers and both the HT-1 and E-1 spectra will be observed. If the first layer does not effectively resist mixing with the solvent for the second layer, there will be significant mixing of the two materials. The PL of the higher energy E-1 will be quenched by the presence of HT-1 and only the PL spectrum of HT-1 will be observed.

In PLT Type 1, facilitation additives to be tested were added to the solution of HT-1 and deposited with HT-1 onto the ITO/glass substrate.

In PLT Type 2, facilitation additives to be tested were added to the solution of HT-1 and deposited with HT-1 onto the ITO/glass substrate. In addition, the deposited layer was capped with a lid during the baking step. The lid was removed, and the second layer was spun coat over the first layer.

In PLT Type 3, a layer of the facilitation additive was formed over the first layer of the test coupon by melting several pieces of facilitation additive, prior to the baking step.

In PLT Type 4, a layer of the facilitation additive was placed on the ground out cavity of a glass lid. The lad was placed over the first layer, with the cavity facing the first layer, during the baking step.

The results of the PLT were evaluated according to the following scale:

5=both HT-1 and E-1 spectra were observed indicating little if any mixing

3=some loss of E-1 spectrum was observed indicating some mixing

1=spectrum was almost completely that of HT-1 indicating significant mixing

OLED Devices (1) Materials

HIJ-1 is an electrically conductive polymer doped with a polymeric fluorinated sulfonic acid.

HT-1 is discussed above

HT-2 is

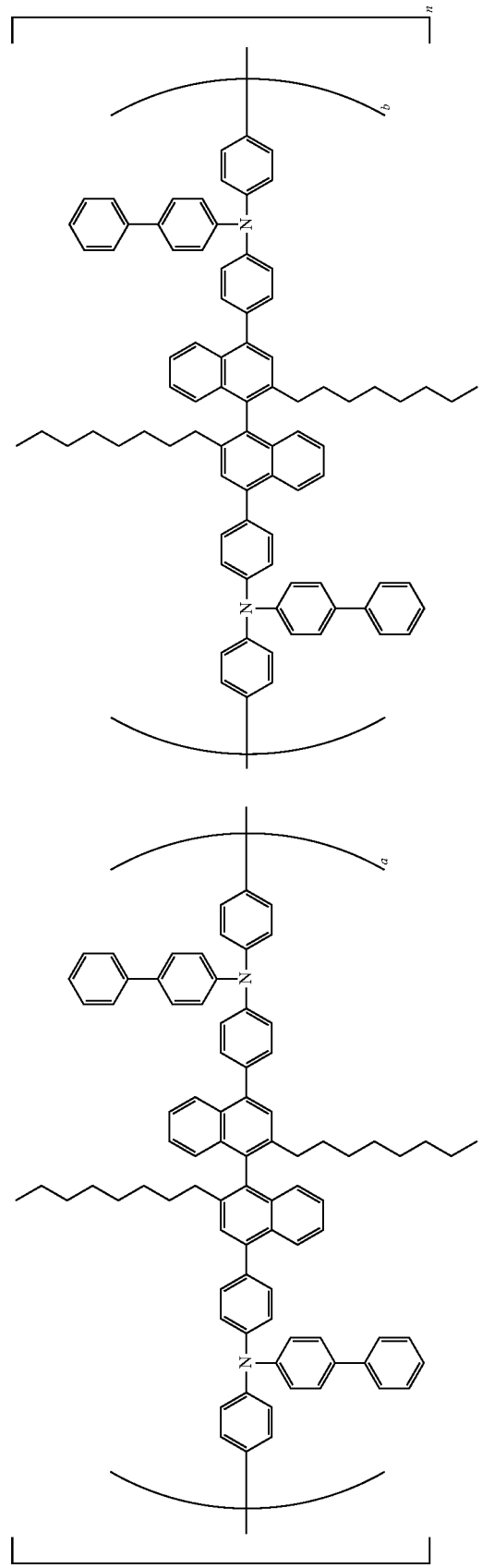

where a:b is about 8.8:1.2; n>10; Mw>100,000. In some embodiments, the ratio a:b is between about 7.5:2.5 and about 10.0:0 (b=0), for example, 8.0:2.0, 9.2:0.8, and between 9.5:0.5 and 10.0:0 (b=0).

HT-3 is

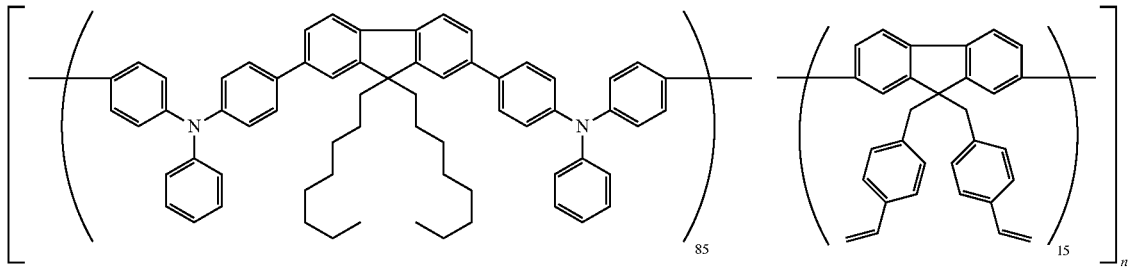

where n>10; Mw>100,000.

Host-1 is a deuterated diaryl anthracene compound.
E-2 is a bis(diarylamino)chrysene.
E-3 is a deuterated bis(diarylamino)chrysene
ET-1 is a quinolate compound.
ET-2 is a diarylfluoranthene compound.
EIJ-1 is a metal fluoride salt.
EIJ-2 is a metal quinolate compound.
The devices had the following structure on a glass substrate:
  anode=ITO (50 nm)
  hole injection layer=HIJ-1 (100 nm)
  hole transport layer=discussed below
  photoactive layer, discussed below (40 nm),
  electron transport layer, discussed below (20 nm)
  electron injection layer ("EIL")/cathode, discussed below, EIL/Al (3.5/100 nm)

(2) Device Fabrication (SCOLEDT)

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission.

The patterned ITO substrates were cleaned and spin-coated with an aqueous dispersion of a hole injection material (HIJ-1). A hole transport layer was formed by spin-coating a solution of hole transport material in a liquid medium. In some examples, a facilitation additive was present in the hole transport solution. The hole transport layer was baked as indicated. The workpieces were then spin-coated with a solution of the photoactive layer materials in methyl benzoate and heated to remove solvent. The workpieces were masked and placed in a vacuum chamber. A layer of electron transport material (ET-1) was deposited by thermal evaporation, followed by a layer of electron injection material (EIJ-1). Masks were then changed in vacuo and a layer of Al was deposited by thermal evaporation. The chamber was vented, and the devices were encapsulated using a glass lid, desiccant, and UV curable epoxy.

(3) Device Characterization

The OLED samples were characterized by measuring their (1) current-voltage (I-V) curves, (2) electroluminescence luminance versus voltage, and (3) electroluminescence spectra versus voltage. All three measurements were performed at the same time and controlled by a computer. The current efficiency of the device at a certain voltage is determined by dividing the electroluminescence luminance of the LED by the current density needed to run the device. The unit is a cd/A. The color coordinates were determined using either a Minolta CS-100 meter or a Photoresearch PR-705 meter.

The effectiveness of the facilitation additive was evaluated by the effect on voltage, efficiency and lifetime. The facilitation additives were rated as follows:
  5=most effective, almost no mixing of layers
  4=effective; very little mixing of layers
  3=moderately effective; some mixing of layers
  2=slightly effective; considerable mixing of layers
  1=no effect; layers are mixed Facilitation Additives

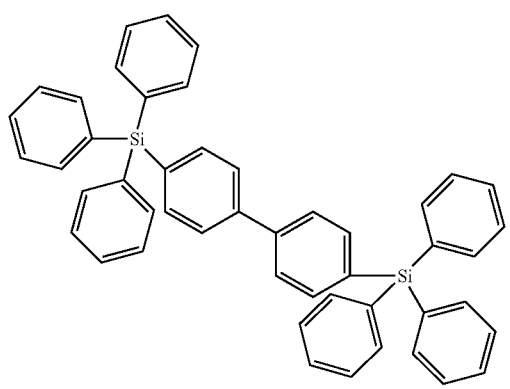

FA-1

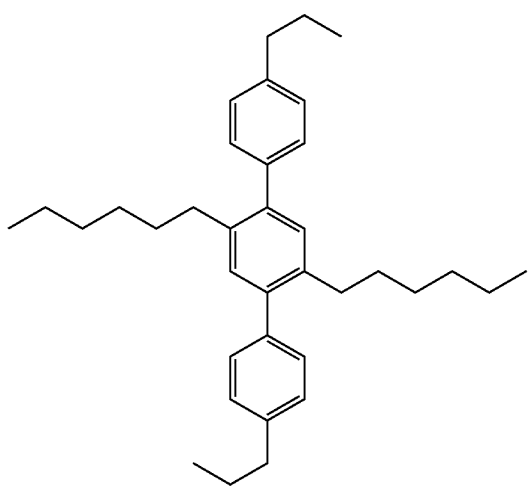

FA-2

-continued
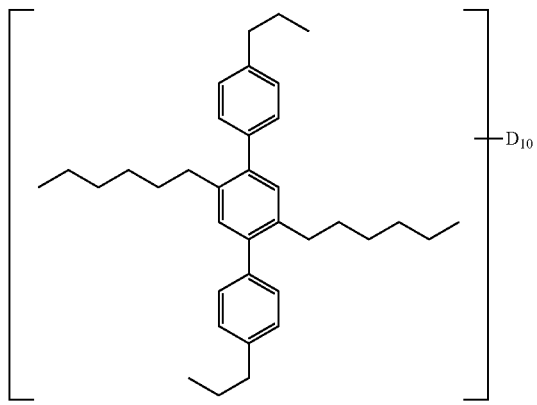
FA-3
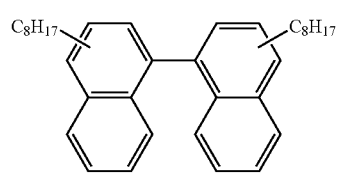
FA-4
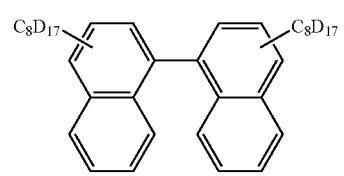
FA-5
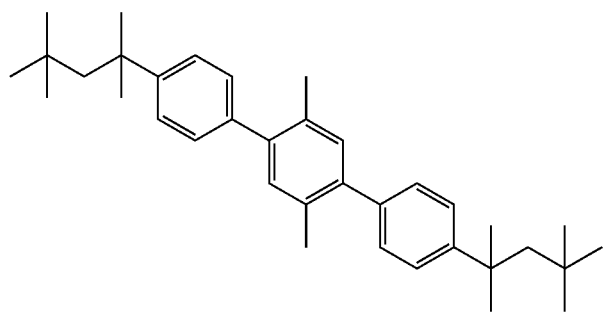
FA-6
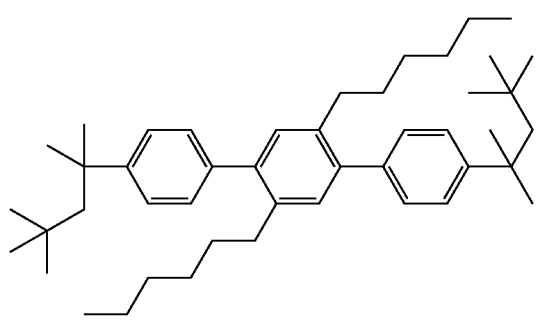
FA-7
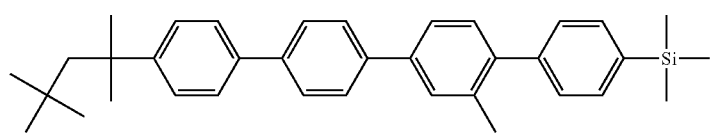
FA-8
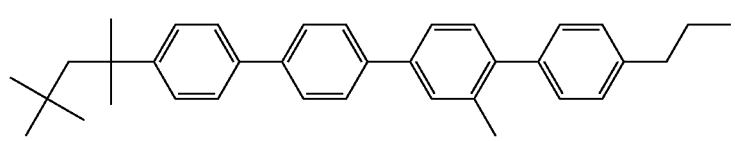
FA-9

-continued
FA-10
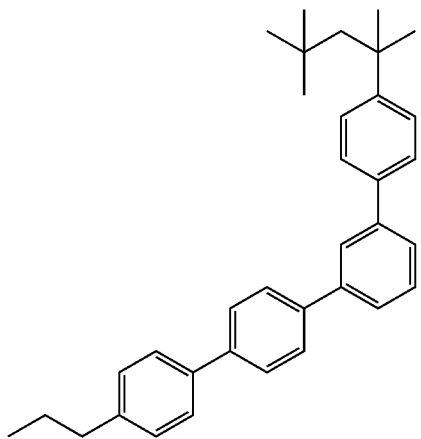
FA-11
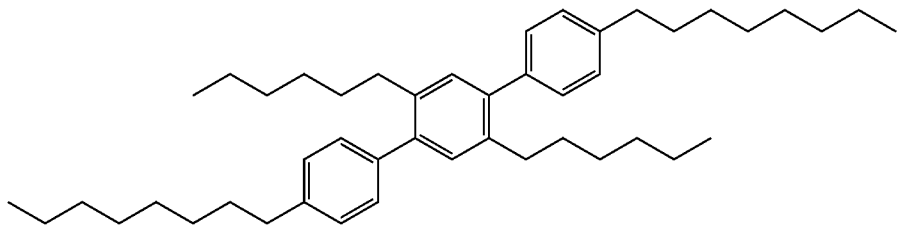
FA-12
FA-13
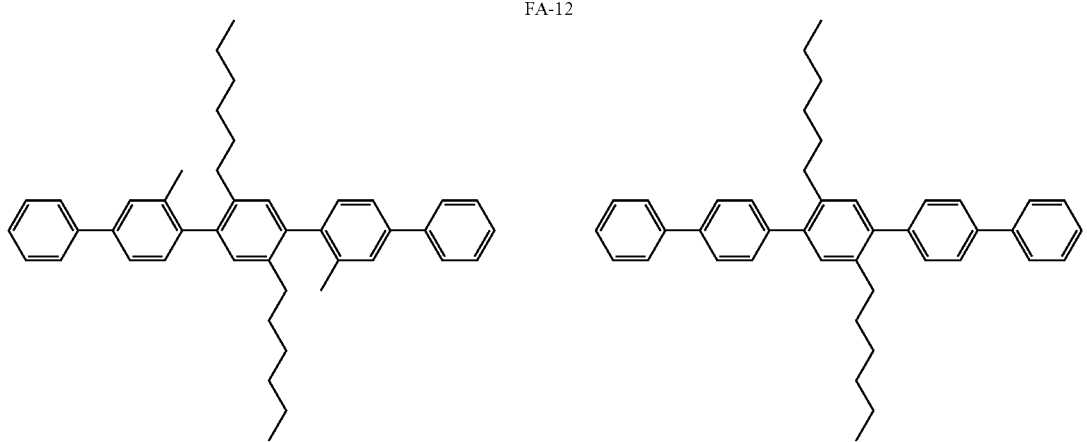
FA-14
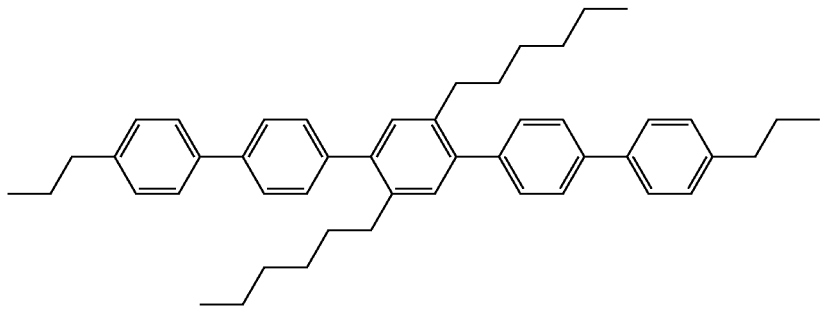

FA-15
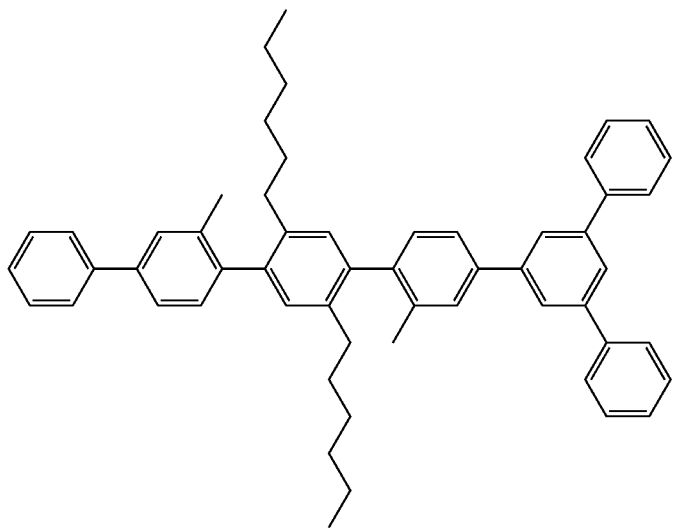
FA-16
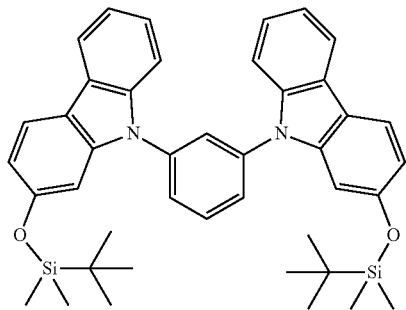
FA-17
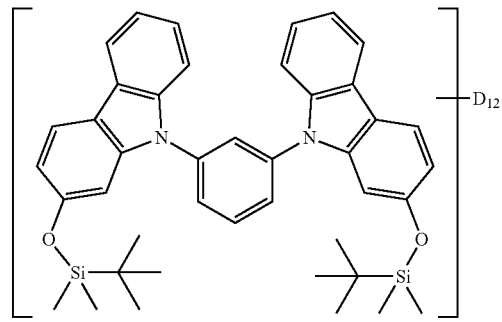
FA-18
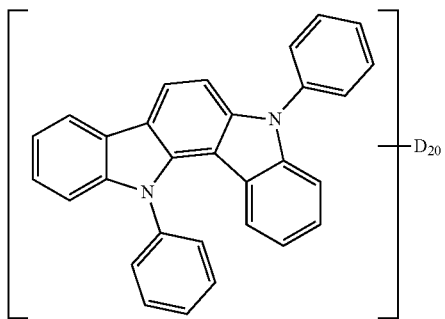
FA-19
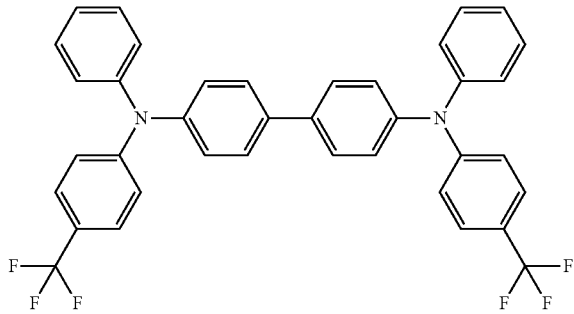

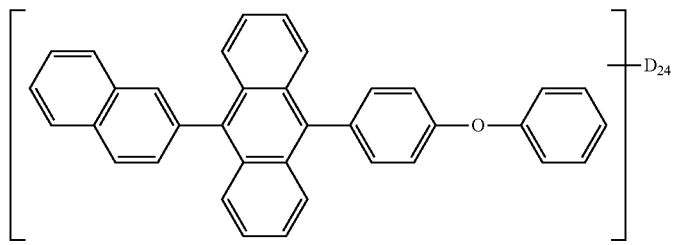
FA-20

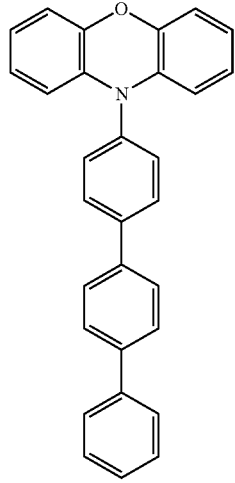
FA-21

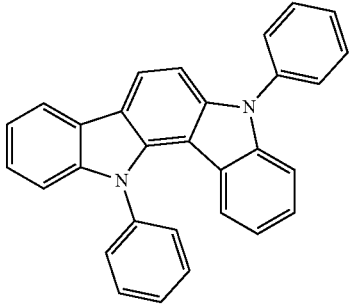
FA-22

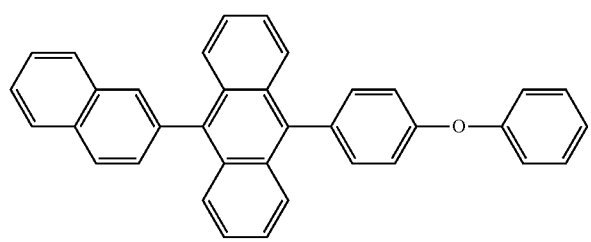
FA-23

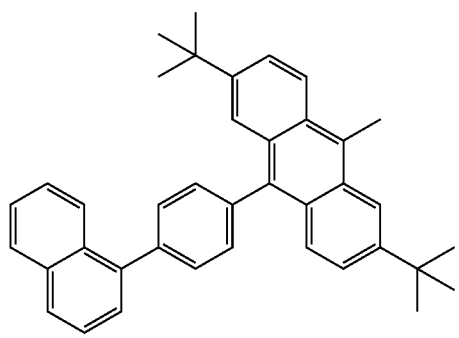
FA-24

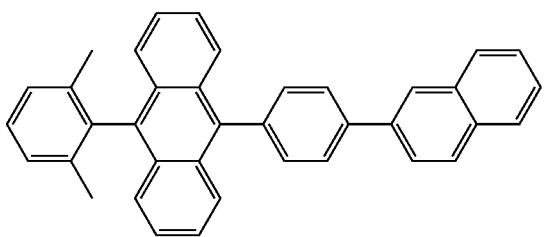
FA-25

Examples 1-10 and Comparative Examples A and B

These examples illustrate the use of the PLT, Type 1, to determine the effectiveness of different facilitation additives when deposited with the hole transport in a liquid medium to form the first layer.

The liquid medium for the hole transport material, HT-1, and additive was toluene. The weight ratio of HT-1 to additive, the baking time, baking temperature, and results are given in Table 1.

TABLE 1

| | PLT results | | | | |
|---|---|---|---|---|---|
| Example | Facilitation Additive | Ratio | Bake Temp. (° C.) | Bake Time (min.) | Results |
| 1 | FA-15 | 9:1 | 250 | 15 | 5 |
| 2 | FA-16 | 7:3 | 230 | 10 | 5 |
| 3 | FA-21 | 7:3 | 230 | 10 | 5 |
| 4 | FA-22 | 7:3 | 230 | 10 | 5 |

TABLE 1-continued

PLT results

| Example | Facilitation Additive | Ratio | Bake Temp. (° C.) | Bake Time (min.) | Results |
|---|---|---|---|---|---|
| 5 | FA-23 | 7:3 | 230 | 10 | 5 |
| 6 | FA-25 | 7:3 | 230 | 10 | 5 |
| 7 | Tri-isodecyl-trimellitate | 7:3 | 230 | 10 | 5 |
| 8 | FA-19 | 7:3 | 230 | 10 | 5 |
| 9 | FA-24 | 7:3 | 230 | 10 | 5 |
| 10 | Trimethyl-1,2,4-benzenetri-carboxylate | 7:3 | 230 | 10 | 3 |
| Comparative A | none | | 230 | 10 | 1 |
| Comparative B | Tetraphenyl-cyclopenta-dieneone | 7:3 | 230 | 10 | 1 |

Ratio is the weight ratio of HT-1 to facilitation additive

Examples 11-12 and Comparative Example C

These examples illustrate the use of tetracontane as a facilitation additive.

In Example 11, the tetracontane was tested according to PLT, Type 2.

In Example 12, the tetracontane was tested according to PLT, Type 4.

In Comparative Example C, the tetracontane was tested according to PLT, Type 1.

The results are given in Table 2 below.

TABLE 2

PLT Results

| Example | PLT | Ratio | Bake Temp. (° C.) | Bake Time (min.) | Results |
|---|---|---|---|---|---|
| Comparative C | Type 1 | 86:14 | 250 | 15 | 1 |
| 11 | Type 2 | 86:14 | 250 | 15 | 3 |
| 12 | Type 4 | | 250 | 15 | 5 |

Ratio is the weight ratio of HT-1 to facilitation additive

Examples 13-25

These examples illustrate the use of the PLT, Type 4. For liquid materials, 2 μl of the facilitation additive were placed in the cavity of the glass lid. Materials with a melting point close to room temperature were melted and then 2 μl of the facilitation additive was placed in the cavity of the glass lid. Solid materials with higher melting points were added directly to the cavity lid in solid form using tweezers (approximately 2-10 mg) and then briefly heated to melt and disperse on the surface of the cavity. The results are given in Table 3.

TABLE 3

PLT results

| Example | Facilitation Additive | Bake Temp. (° C.) | Bake Time (min.) | Results |
|---|---|---|---|---|
| 13 | Hexadecane | 250 | 15 | 5 |
| 14 | Heptadecane | 250 | 15 | 5 |

TABLE 3-continued

PLT results

| Example | Facilitation Additive | Bake Temp. (° C.) | Bake Time (min.) | Results |
|---|---|---|---|---|
| 15 | Dodecane | 250 | 15 | 5 |
| 16 | Tetradecane | 250 | 15 | 5 |
| 17 | Octadecane | 250 | 15 | 5 |
| 18 | Icosane | 250 | 15 | 5 |
| 19 | Docosane | 250 | 15 | 5 |
| 20 | Tetracosane | 250 | 15 | 5 |
| 21 | Octacosane | 250 | 15 | 5 |
| 22 | Dotriacontane | 250 | 15 | 5 |
| 23 | Mineral oil | 250 | 15 | 5 |
| 24 | Pentacontane | 250 | 15 | 5 |
| 25 | Hexacontane | 250 | 15 | 5 |

Examples 26-27

These examples illustrate the use of hexatriacontane as a facilitation additive.

In Example 26, the hexatriacontane was tested according to PLT, Type 3.

In Example 27, the hexatriacontane was tested according to PLT, Type 4.

The results are given in Table 4 below.

TABLE 4

PLT Results

| Example | PLT | Bake Temp. (° C.) | Bake Time (min.) | Results |
|---|---|---|---|---|
| 26 | Type 3 | 250 | 15 | 5 |
| 27 | Type 4 | 250 | 15 | 5 |

Examples 28-42 and Comparative Examples D and E

These examples illustrate the use of the SCOLEDT to determine the effectiveness of different facilitation additives when deposited with the hole transport in a liquid medium to form the first layer.

Devices were made as described above with a facilitation additive present with the hole transport material when the hole transport material was deposited.

In Example 28 and Comparative Example D, the hole transport layer had a final thickness of 20 nm; the photoactive layer was Host-1:E-2; the electron transport material was ET-1; the electron injection material was EIJ-1.

In Examples 29-42 and Comparative Example E, the hole transport layer had a final thickness of 100 nm; the photoactive layer was Host-1:E-3; the electron transport material was ET-2; the electron injection material was EIJ-2.

The materials, amounts, time, temperature and results are given in Table 5 below.

TABLE 5

SCOLEDT Results

| Ex. | HTM | Facilitation Additive | Ratio | Bake Temp. (° C.) | Bake Time (min.) | Results |
|---|---|---|---|---|---|---|
| Comp. D | HT-2 | None | | 250 | 30 | 1 |
| Comp. E | HT-1 | None | | 250 | 30 | 1 |

TABLE 5-continued

SCOLEDT Results

| Ex. | HTM | Facilitation Additive | Ratio | Bake Temp. (° C.) | Bake Time (min.) | Results |
|---|---|---|---|---|---|---|
| 28 | HT-2 | FA-1 | 6:4 | 250 | 30 | 4 |
| 29 | HT-1 | FA-12 | 7:3 | 250 | 20 | 5 |
| 30 | HT-1 | FA-13 | 7:3 | 250 | 10 | 5 |
| 31 | HT-1 | FA-14 | 95:5 | 250 | 10 | 5 |
| 32 | HT-1 | FA-15 | 95:5 | 250 | 30 | 5 |
| 33 | HT-1 | FA-4 | 7:3 | 225 | 10 | 5 |
| 34 | HT-1 | FA-2 | 6:4 | 225 | 10 | 5 |
| 35 | HT-1 | FA-6 | 6:4 | 225 | 10 | 4 |
| 36 | HT-1 | FA-7 | 8:2 | 225 | 5 | 4 |
| 37 | HT-1 | FA-8 | 7:3 | 225 | 10 | 5 |
| 38 | HT-1 | FA-9 | 7:3 | 225 | 10 | 5 |
| 39 | HT-1 | FA-10 | 8:2 | 225 | 10 | 5 |
| 40 | HT-1 | FA-11 | 85:15 | 225 | 10 | 5 |
| 41 | HT-1 | FA-2 | 6:4 | 205 | 10 | 5 |
| 42 | HT-1 | FA-2 | 6:4 | 195 | 10 | 4 |

HTM = hole transport material;
Ratio = the weight ratio of the hole transport material to the facilitation additive Examples 43-50 and Comparative Examples F-H These examples illustrate the use of facilitation additives, where the additives are present adjacent to the hole transport layer during the baking step, using the SCOLEDT.

The hole transport materials was HT-1 and the hole transport layer had a final thickness of 100 nm; the photoactive layer was Host-1:E-3; the electron transport material was ET-2; the electron injection material was EIJ-2.

Devices were made as described above with no facilitation additive in the hole transport layer. A facilitation additive was placed in the ground out cavity of a glass lid and placed over the deposited hole transport material for the baking step, such that the cavity side with the facilitation additive was facing the hole transport material.

The facilitation additives, amounts, time, temperature and results are given in Table 6 below.

TABLE 6

SCOLEDT Results

| Ex. | Facilitation Additive | Amount | Bake Temp. (° C.) | Bake Time (min.) | Results |
|---|---|---|---|---|---|
| Comp. F | None | | 250 | 15 | 1 |
| Comp. G | Water | 8 μl | 230 | 10 | 1 |
| Comp. H | Propylene glycol | 4 μl | 230 | 10 | 1 |
| 43 | Hexadecane | 2 μl | 250 | 15 | 5 |
| 44 | Anisole | 2 μl | 250 | 15 | 4 |
| 45 | Tetraline | 2 μl | 250 | 15 | 4 |
| 46 | 3-Ethylbiphenyl | 2 μl | 250 | 15 | 4 |
| 47 | 1-Phenylnapthalene | 2 μl | 250 | 15 | 4 |
| 48 | Diethyl phthalate | 2 μl | 250 | 15 | 4 |
| 49 | Octadecane | 4 μl | 230 | 10 | 5 |
| 50 | Methyl benzoate | 4 μl | 230 | 10 | 4 |

Examples 51-54 and Comparative Examples I-J

These examples illustrate the use of facilitation additives with a crosslinkable hole transport material, HT-3.

When using a crosslinkable material in the hole transport layer, one can gauge the resistance to dissolution by a subsequent layer by studying the film retention when exposed to a solvent which would normally dissolve the entire layer if not crosslinked. In this study films of a crosslinkable hole transport polymer, HT-3, with and without a facilitation additive, FA-2, were spun cast onto a glass/ITO substrate. The films were baked and then the thickness was measured using a KLA-Tencor P15 profilometer. After profilometry each sample was subjected to an anisole rinse. The method of the anisole rinse was as follows: a substrate was placed in a spincoater where 1 ml of anisole was puddled on the surface of the substrate for 30 s, the sample was then rotated at 2000 rpm while 40 ml of anisole was dispensed onto the substrate over the course of 60 s, the sample was then allowed to spin to dryness. After the anisole rinse the film thickness was measured once again with the profilometer. A retention number is a comparison of the final film thickness as a percentage of the initial film thickness. The presence of a facilitation additive was seen to result in a greater amount of retention of the hole transport film at multiple temperatures, as shown in Table 7.

TABLE 7

Results

| Example | Facilitation Additive | Bake Temp. (° C.) | Bake Time (min.) | Retention |
|---|---|---|---|---|
| Comp. I | None | 200 | 10 | 34% |
| Comp. J | None | 175 | 10 | 0% |
| 51 | 20% FA-2 | 200 | 10 | 43% |
| 52 | 30% FA-2 | 200 | 10 | 47% |
| 53 | 20% FA-2 | 175 | 10 | 11% |
| 54 | 30% FA-2 | 175 | 10 | 15% |

The present application includes an electroactive system for forming an electroactive layer, comprising (a) a first electroactive material; (b) a facilitation additive; and (c) a first liquid medium; wherein the facilitation additive is present during baking in an amount sufficient to enable the electroactive layer made therefrom to effectively resist mixing with a second liquid medium applied thereover after the electroactive system is deposited onto a workpiece and baked at a temperature less than 350° C. for a predetermined time.

In some embodiments, the electroactive material comprises at least one photoactive material and at least one host material. In some embodiments, the electroactive material comprises hole transport material. In some embodiments, the facilitation additive has a boiling point of 150° C. or greater. In some embodiments, wherein the facilitation additive has a vapor pressure at 225° C. that is in a range of $10^{-3}$ Pa to 40 Pa. In some embodiments, the facilitation additive is a small molecule having a molecular weight less than 2000.

In some embodiments, the facilitation additive has Formula VIII

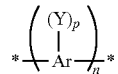

(VIII)

wherein:
Ar is the same or different at each occurrence and is an aryl group or deuterated aryl group having 3-60 ring carbons;

Y is the same or different at each occurrence and is selected from the group consisting of D, alkyl, alkoxy, aryl, aryloxy, carboxylic ester, silyl, siloxane, amino, carbazolyl, deuterated alkyl, deuterated alkoxy, deuterated aryl, deuterated aryloxy, deuterated carboxylic ester, deuterated silyl, deuterated siloxane, deuterated amino, and deuterated carbazolyl, where Y groups on adjacent carbons may be joined together to form a fused 5- or 6-membered aliphatic ring;

n is an integer greater than 0;

p is an integer greater than 0; and

* represents a point of attachment, H, D, halide, aryl, or deuterated aryl.

The present application includes a process for forming an electroactive layer, comprising (i) depositing a first electroactive composition onto a workpiece, to form a deposited layer, wherein the first electroactive composition comprises a first electroactive material, a facilitation additive, and a first liquid medium; (ii) baking the deposited layer at a temperature less than 350° C. for a predetermined time; and (iii) depositing over the first electroactive layer a second electroactive composition comprising a second electroactive material in a second liquid medium; wherein the facilitation additive is present in an amount sufficient to enable the first electroactive layer to effectively resist mixing with the second liquid medium.

In some embodiments, the predetermined time is sufficient to evaporate substantially all of the first liquid medium. In some embodiments, the facilitation additive has a boiling point of 150° C. or greater. In some embodiments, the facilitation additive has a vapor pressure at 225° C. that is in a range of $10^{-3}$ Pa to 40 Pa. In some embodiments, wherein the facilitation additive is a small molecule having a molecular weight less than 2000. In some embodiments, wherein the electroactive material comprises at least one photoactive material and at least one host material. In some embodiments, the electroactive material comprises hole transport material.

The present application includes a process for forming an electroactive layer, comprising (i) depositing a first electroactive composition onto a workpiece to form a deposited layer, wherein the first electroactive composition comprises a first electroactive material and a first liquid medium; (ii) baking the deposited layer in the presence of a facilitation additive, where the baking is carried out at a temperature less than 350° C. for a predetermined time; and (iii) depositing over the first electroactive layer a second electroactive composition comprising a second electroactive material in a second liquid medium; wherein the facilitation additive is present in an amount sufficient to enable the first electroactive layer to effectively resist mixing with the second liquid medium.

In some embodiments, the predetermined time is sufficient to evaporate substantially all of the first liquid medium. In some embodiments, the facilitation additive has a boiling point of 150° C. or greater. In some embodiments, the facilitation additive has a vapor pressure at 225° C. that is in a range of $10^{-3}$ Pa to 40 Pa. In some embodiments, wherein the facilitation additive is a small molecule having a molecular weight less than 2000. In some embodiments, wherein the electroactive material comprises at least one photoactive material and at least one host material. In some embodiments, the electroactive material comprises hole transport material.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner, slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. A composition comprising a mixture of:
   (a) a first electroactive material;
   (b) a facilitation additive having no crosslinkable groups; and
   (c) a first liquid medium;
   wherein the facilitation additive is present during baking in an amount sufficient to enable an electroactive layer made from the composition to effectively resist mixing with a second liquid medium applied over the electroactive layer after the composition is deposited onto a workpiece and baked at a temperature less than 350° C. for a predetermined time;
   wherein the facilitation additive has a vapor pressure at 225° C. that is in a range of $10^{-3}$ Pa to 40 Pa.

2. The composition of claim 1, wherein the electroactive material comprises at least one photoactive material and at least one host material.

3. The composition of claim 1, wherein the electroactive material comprises hole transport material.

4. The composition of claim 1, wherein the facilitation additive is a small molecule having a molecular weight less than 2000.

5. The composition of claim 1, wherein the facilitation additive has a boiling point of 150° C. or greater.

* * * * *